(12) United States Patent
Yasui

(10) Patent No.: US 10,866,231 B2
(45) Date of Patent: Dec. 15, 2020

(54) BIOLOGICAL INFORMATION DETECTION SENSOR FEEDING APPARATUS

(71) Applicant: PHC Holdings Corporation, Tokyo (JP)

(72) Inventor: Shinichi Yasui, Toon (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 16/006,313

(22) Filed: Jun. 12, 2018

(65) Prior Publication Data
US 2018/0289300 A1 Oct. 11, 2018

Related U.S. Application Data

(62) Division of application No. 15/649,083, filed on Jul. 13, 2017, now Pat. No. 10,016,150, which is a
(Continued)

(30) Foreign Application Priority Data

Sep. 14, 2011 (JP) .................................. 2011-200485

(51) Int. Cl.
| | |
|---|---|
| *G01N 33/487* | (2006.01) |
| *G01N 35/00* | (2006.01) |
| *A61B 5/145* | (2006.01) |

(52) U.S. Cl.
CPC ... *G01N 33/48764* (2013.01); *A61B 5/14532* (2013.01); *G01N 35/00009* (2013.01); *G01N 2035/00019* (2013.01)

(58) Field of Classification Search
CPC ..... A61B 5/14532; G01N 2035/00019; G01N 33/48764; G01N 35/00009
See application file for complete search history.

(56) References Cited

U.S. PATENT DOCUMENTS

| | | |
|---|---|---|
| 3,260,413 A | 7/1966 | Natelson |
| 2002/0188224 A1 | 12/2002 | Roe et al. |

(Continued)

FOREIGN PATENT DOCUMENTS

| | | |
|---|---|---|
| CN | 1456891 | 11/2003 |
| CN | 101432623 | 5/2009 |

(Continued)

OTHER PUBLICATIONS

JP 2001-281199, Oct. 10, 2001, translation of specification.
(Continued)

*Primary Examiner* — Samuel P Siefke
(74) *Attorney, Agent, or Firm* — Hamre, Schumann, Mueller & Larson, P.C.

(57) ABSTRACT

The biological information detection sensor supply device is provided with a main body case having a supply port to which a biological information measurement device can be attached, a housing unit for housing a biological information detection sensor and a sensor supply film including a cover film and a holding film for sandwiching the biological information detection sensor, and a supply unit for supplying the biological information detection sensor from the housing unit to the supply port. The supply unit supplies the biological information detection sensor to the supply port, and separates the holding film and the cover film from the sensor supply film in a state before the biological information detection sensor is supplied to the supply port. At the supply unit, the biological information detection sensor supplied to the supply port is fitted to the biological information measurement device fitted to the supply port.

7 Claims, 17 Drawing Sheets

Related U.S. Application Data division of application No. 14/236,247, filed as application No. PCT/JP2012/005863 on Sep. 14, 2012, now abandoned.

(56) References Cited

U.S. PATENT DOCUMENTS

| | | |
|---|---|---|
| 2003/0211619 A1 | 11/2003 | Olson et al. |
| 2005/0245954 A1 | 11/2005 | Roe et al. |
| 2006/0078469 A1 | 4/2006 | Dechant et al. |
| 2007/0038150 A1 | 2/2007 | Calasso et al. |
| 2009/0095641 A1 | 4/2009 | List et al. |

FOREIGN PATENT DOCUMENTS

| | | |
|---|---|---|
| JP | 2001-141686 | 5/2001 |
| JP | 2001-281199 | 10/2001 |
| JP | 2002-310972 | 10/2002 |
| JP | 2003-42994 | 2/2003 |
| JP | 2003-215085 | 7/2003 |
| JP | 2004-130063 | 4/2004 |
| JP | 2007-535351 | 12/2007 |
| JP | 2009-535630 | 10/2009 |

OTHER PUBLICATIONS

Partial Supplementary European Search Report issued in corresponding European Application No. 12831599.1, dated Jan. 5, 2015 (6 pages).

English translation of Search Report; Chinese Office Action issued in corresponding Chinese Application No. 201280035914.0, dated Sep. 23, 2014 (2 pages).

BIOLOGICAL INFORMATION DETECTION SENSOR FEEDING APPARATUS

TECHNICAL FIELD

The present invention relates to a biological information detection sensor feeding apparatus. More specifically, the present invention relates to a biological information detection sensor feeding apparatus that feeds a biological information detection sensor such as a blood glucose sensor, for example.

BACKGROUND ART

A conventional biological information detection sensor feeding apparatus includes, for example, a body case having a feeding opening for a test element (an example of a biological information detection sensor); a storage section that stores a strip-shaped sensor feeding film in the body case; and a feeding section that feeds a predetermined length of the sensor feeding film from the storage section to the feeding opening. The feeding section is configured to feed a predetermined length of the sensor feeding film to the feeding opening, and immediately before the feeding opening, peel a covering film from a surface of a holding film constituting the sensor feeding film (see PTL 1).

CITATION LIST

Patent Literature

PTL 1
Japanese Unexamined Patent Application Publication (Translation of PCT Application) No. 2007-535351

SUMMARY OF INVENTION

Technical Problem

In the conventional configuration, one biological information detection sensor (an example of a test element) is fed to the feeding opening. However, when taking the biological information detection sensor fed to the feeding opening, the user may unwittingly contaminate the biological information detection sensor by dropping.

Since biological information detection sensors are used for measuring biological samples, it is undesirable to a contaminated biological information detection sensor. Consequently, it is necessary to take out a new sensor from the biological information detection sensor feeding apparatus, again. Thus, the conventional biological information detection sensor feeding apparatus suffers from poor usability. Hence, an object of the present invention is to provide a biological information detection sensor feeding apparatus that is easy to use.

Solution to Problem

To achieve the above-described object, a biological information detection sensor feeding apparatus according to Embodiment 1 of the present invention includes: a body case having a feeding stage; a storage section that stores a strip-shaped sensor feeding film in the body case, the sensor feeding film including a biological information detection sensor, and a holding film and a covering film that sandwich the biological information detection sensor; and a feeding section that feeds the biological information detection sensor from the storage section to the feeding stage. The feeding section is configured to feed the holding film of the sensor feeding film and the biological information detection sensor to the feeding stage, and peel the covering film from the sensor feeding film before feeding the biological information detection sensor to the feeding stage, and is configured to wind the holding film fed to the feeding stage. The feeding stage inclines downward along a feeding direction of the sensor feeding film.

To achieve the object, a biological information detection sensor feeding apparatus according to Embodiment 2 of the present invention includes: a body case having a feeding opening configured such that a biological information measurer can be attached thereto; a storage section that stores a strip-shaped sensor feeding film in the body case, the sensor feeding film including a biological information detection sensor, and a holding film and a covering film that sandwich the biological information detection sensor; and a feeding section that feeds the biological information detection sensor from the storage section to the feeding opening. The feeding section is configured to feed the biological information detection sensor to the feeding opening, and separate the holding film and the covering film from the sensor feeding film before feeding the biological information detection sensor to the feeding opening. The feeding section is configured to load the biological information detection sensor fed to the feeding opening, into the biological information measurer attached to the feeding opening.

To achieve the above-described object, a biological information detection sensor feeding apparatus according to Embodiment 3 of the present invention includes: a measuring section that measures biological information; a body case having a loading opening; a storage section that stores a strip-shaped sensor feeding film in the body case, the sensor feeding film including a biological information detection sensor, and a holding film and a covering film that sandwich the biological information detection sensor; and a feeding section that feeds the biological information detection sensor from the storage section to the loading opening. The feeding section is configured to feed the biological information detection sensor to the loading opening, and separate the holding film and the covering film from the sensor feeding film before feeding the biological information detection sensor to the loading opening. The loading opening includes a connector connected with the measuring section and the biological information detection sensor includes a connecting electrode, and the feeding section is configured to feed the biological information detection sensor to the loading opening such that the connecting electrode of the biological information detection sensor is electrically connected with the connecter of the loading opening.

Advantageous Effects of Invention

In accordance with a biological information detection sensor feeding apparatus according to the present invention, it is possible to easily load a biological information detection sensor into a biological information measurer and to simplify the measurement of biological information.

DESCRIPTION OF EMBODIMENTS

Hereinafter, an embodiment of the present invention will be described with reference to the accompanying drawings.

Embodiment 1

Figure 1:
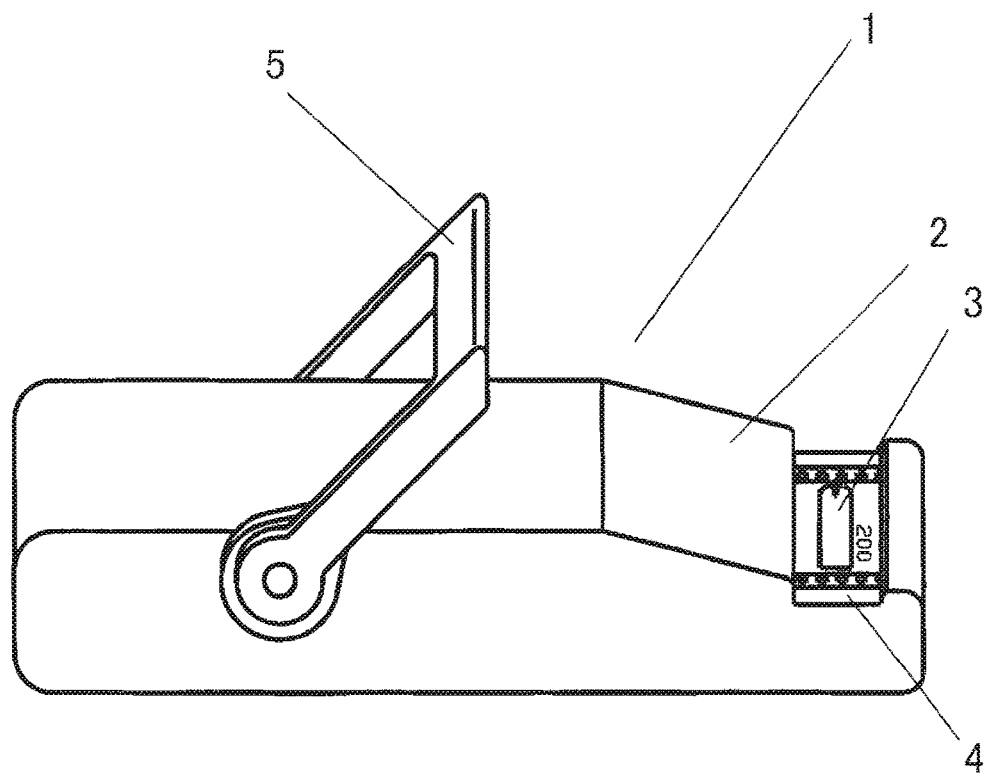
FIG. 1 is a perspective diagram of a biological information detection sensor feeding apparatus according to Embodiment 1.

FIG. 1 shows biological information detection sensor feeding apparatus 1. A user of biological information detection sensor feeding apparatus 1 is a nurse in a hospital, for example. Biological information detection sensor feeding apparatus 1 has body case 2 molded in an approximately cuboidal shape, and feeding stage 4 provided on the upper surface of the front-end side of body case 2. A biological information detection sensor (for example, blood glucose sensor 3) is fed to feeding stage 4.

Operating lever 5 is provided at the rear side of body case 2. By an operation of operating lever 5, blood glucose sensors 3 can be fed to feeding stage 4 one by one.

Figure 2:
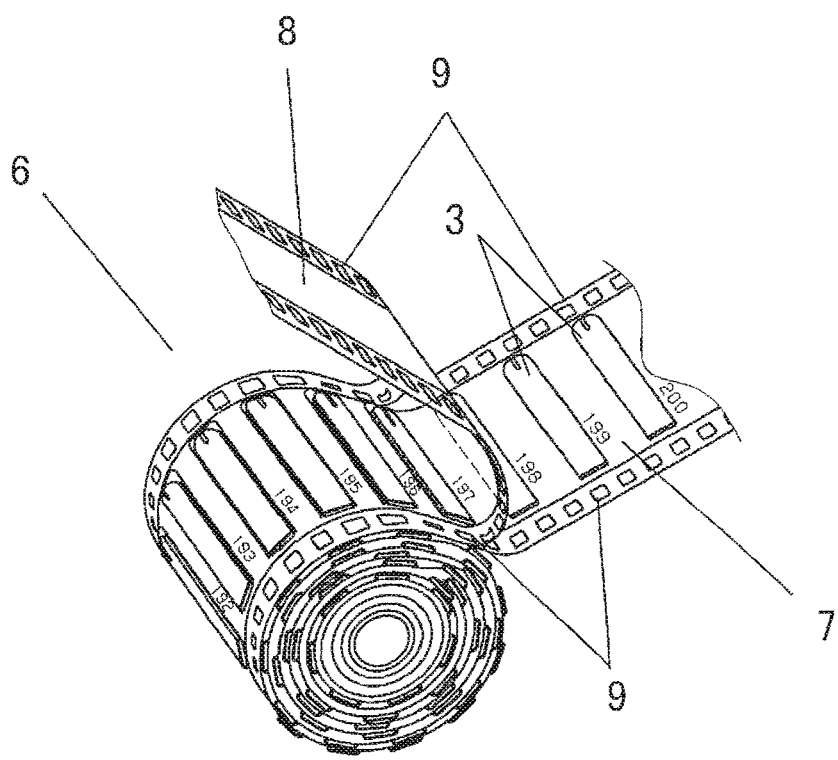
FIG. 2 is a perspective diagram of a roll of a sensor feeding film of the biological information detection sensor feeding apparatus according to Embodiment 1.

As shown in FIG. 2, blood glucose sensor 3 is stored in strip-shaped sensor feeding film 6. Sensor feeding film 6 includes strip-shaped holding film 7 and strip-shaped covering film 8 that covers a surface of holding film 7.

Blood glucose sensor 3 is stored between strip-shaped holding film 7 and strip-shaped covering film 8. That is, on the surface of holding film 7, multiple (in the embodiment, 200) blood glucose sensors 3 are arranged at a predetermined interval along the longitudinal direction of holding film 7. The longitudinal direction of stored blood glucose sensors 3 is orthogonal to the longitudinal direction of holding film 7, but is not particularly limited.

On the surface of holding film 7, discrimination information is indicated in the vicinity of each blood glucose sensor 3. The discrimination information is, for example, the holding number of each blood glucose sensor 3. The holding numbers, which are given in the arrangement order of blood glucose sensors 3, may be in the descending order (for example, from 200 to 1), or may be in the ascending order (for example, from 1 to 200).

At both ends in the direction orthogonal to the longitudinal direction of sensor feeding film 6, there are provided feed guide holes 9 for feeding a predetermined length of sensor feeding film 6 to feeding stage 4 in FIG. 1.

Figure 3A:
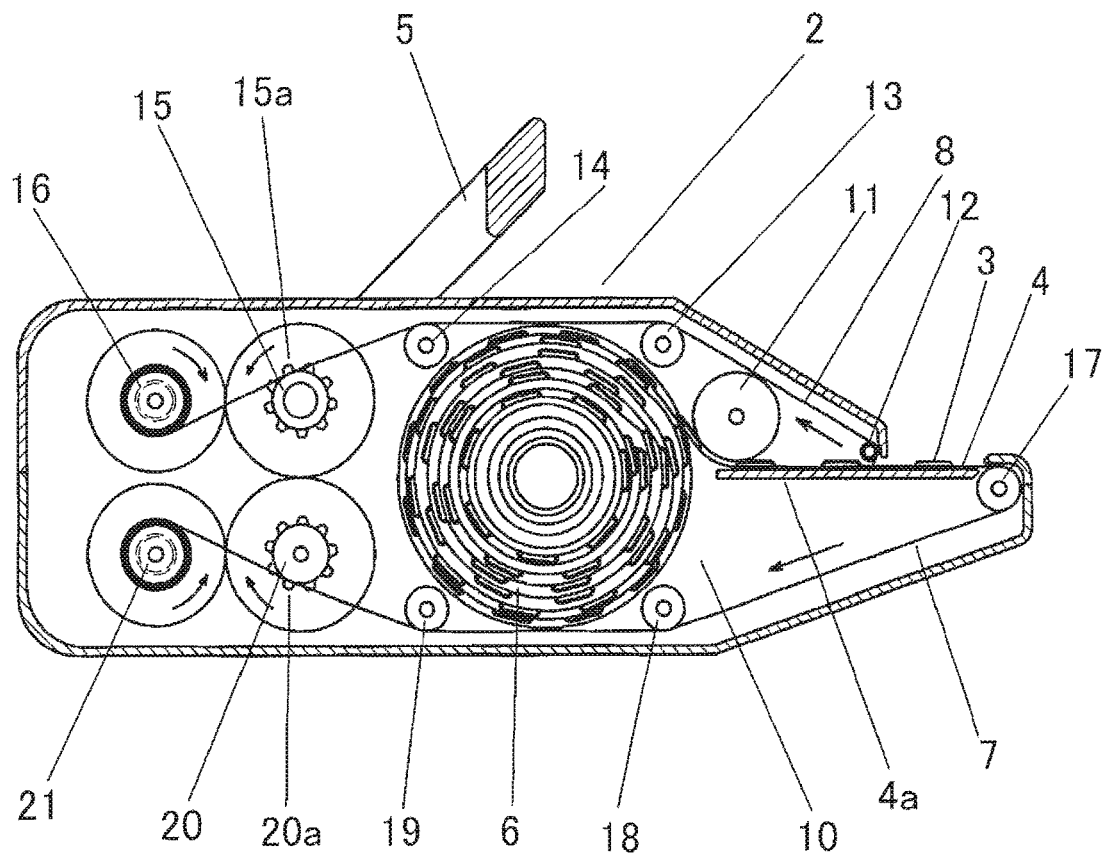
FIG. 3A is a lateral cross-sectional diagram of the biological information detection sensor feeding apparatus according to Embodiment 1.
Figure 3B:
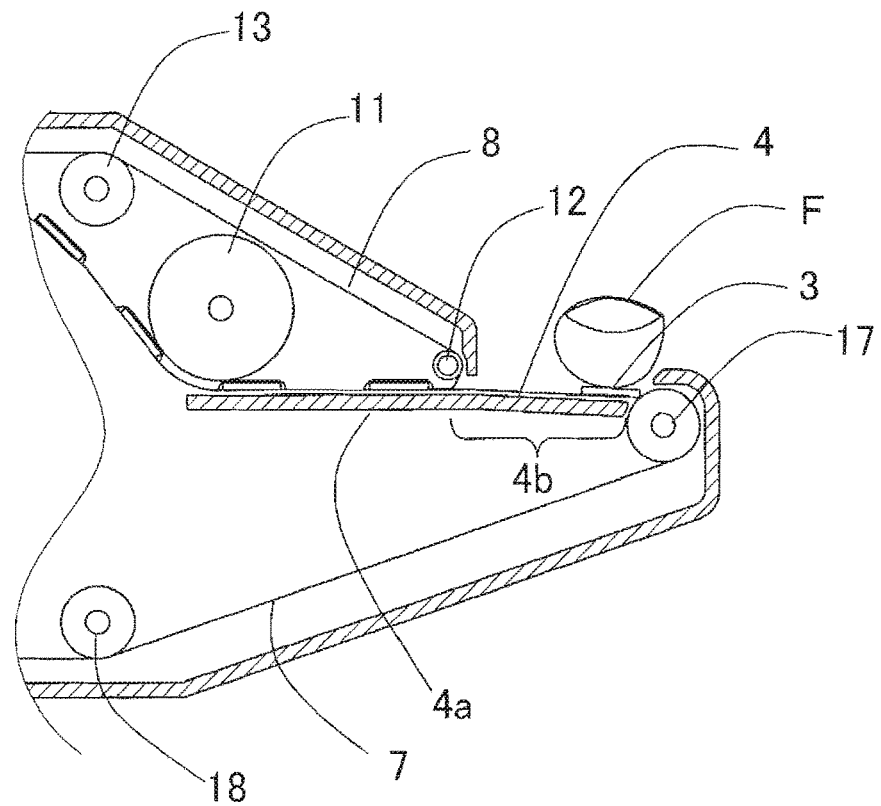
FIG. 3B is an enlarged lateral cross-sectional diagram of the principal part around a feeding stage of the biological information detection sensor feeding apparatus according to Embodiment 1.

FIG. 3A is a cross-sectional diagram of biological information detection sensor feeding apparatus 1 when body case 2 is viewed in the lateral direction; FIG. 3B is an enlarged cross-sectional diagram of biological information detection sensor feeding apparatus 1 when the principal part around feeding stage 4 of body case 2 is viewed in the lateral direction; and FIG. 4 is a perspective diagram of biological information detection sensor feeding apparatus 1 when body case 2 is viewed from the upper surface side.

As shown in FIG. 3A, a roll of sensor feeding film 6 is stored in storage section 10 provided in the interior of body case 2. Storage section 10 only has to be positioned near the center of the interior of body case 2. Preferably, sensor feeding film 6 is loosely wound in a roll so that blood glucose sensor 3 held in sensor feeding film 6 is not damaged.

Figure 4:
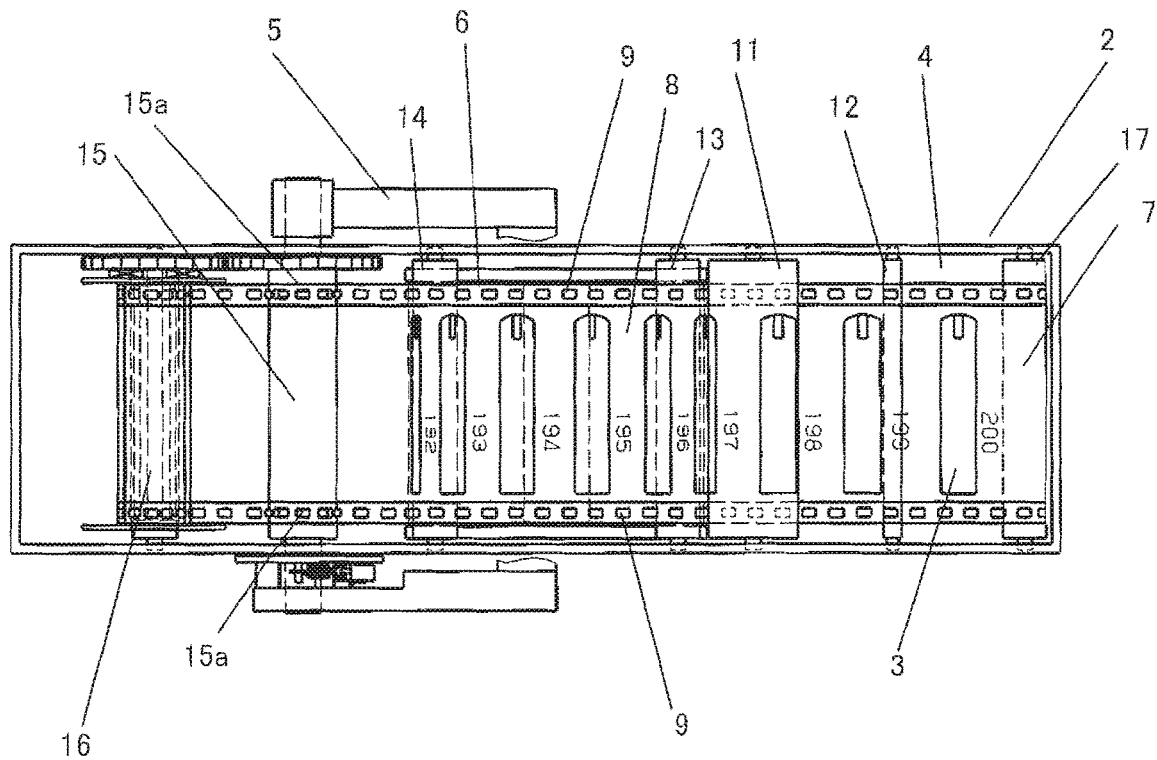
FIG. 4 is a perspective top diagram of the biological information detection sensor feeding apparatus according to Embodiment 1.

As shown in FIG. 3A and FIG. 4, the roll of sensor feeding film 6 is disposed such that the unwinding direction of the roll is oriented to feeding stage 4 in the vicinity of the front-end of body case 2. As shown in FIG. 3A, sensor feeding film 6 is fed to feeding stage 4. In sensor feeding film 6 to be fed, holding film 7, blood glucose sensor 3 and covering film 8, from the bottom in the drawing, are sequentially laminated.

Feeding stage 4 is connected with guiding section 4a. Guiding section 4a is a board within body case 2, and is positioned between storage section 10 and feeding stage 4. Guiding section 4a is a board for guiding sensor feeding film 6 to feeding stage 4.

Cylindrical pressing pulley 11 is disposed above guiding section 4a in the vicinity of storage section 10. The axial length of pressing pulley 11 is greater than the short-directional width of sensor feeding film 6. Thereby, pressing pulley 11 can press the whole of the short-directional width of sensor feeding film 6 onto guiding section 4a.

In the interior of body case 2, cylindrical separating pulley 12 is provided above guiding section 4a in the vicinity of feeding stage 4. Separating pulley 12 separates covering film 8 from sensor feeding film 6. The separated covering film is returned upward and subsequently rearward, and through cylindrical guiding pulleys 13, 14 and cylindrical driving reel 15, is wound by winding reel 16. As understood from FIG. 4, the axis-directional lengths of separating pulley 12, guiding pulleys 13, 14 and driving reel 15 are longer than the short-directional width of sensor feeding film 6.

Thus, blood glucose sensor 3 uncovered on the surface of holding film 7 is fed to feeding stage 4. The board area of feeding stage 4 is greater than the area of blood glucose sensor 3. Thereby, blood glucose sensor 3 can be stably held on feeding stage 4. Blood glucose sensor 3 held on feeding stage 4 is obtained by a user.

As shown in FIG. 3A, in the interior of body case 2, cylindrical returning pulley 17 is provided downstream of feeding stage 4 (downstream side in the feeding direction of sensor feeding film 6). Holding film 7 of sensor feeding film 6 is returned downward and subsequently rearward by returning pulley 17, and through cylindrical guiding pulleys 18, 19 and cylindrical driving reel 20, is wound by winding reel 21. The axial lengths of returning pulley 17, guiding pulleys 18, 19 and driving reel 20 are longer than the short-directional width of sensor feeding film 6.

Driving projections 15a, 20a are provided at both ends respectively of driving reels 15, 20. Driving projections 15a, 20a engage with feed guide holes 9 provided at both ends of sensor feeding film 6. Driving reels 15, 20 are coupled with operating lever 5.

Thus, a winding mechanism for covering film 8 of sensor feeding film 6 is constituted by operating lever 5, winding reel 16, driving reel 15, guiding pulleys 14, 13 and separating pulley 12. A winding mechanism for holding film 7 of sensor feeding film 6 is constituted by operating lever 5, winding reel 21, driving reel 20, guiding pulleys 19, 18 and returning pulley 17. The winding mechanism for covering film 8 and the winding mechanism for holding film 7 are constituent members of the feeding section that feeds a biological information detection sensor.

Winding reel 16 that constitutes the winding mechanism for covering film 8 is provided so as to be connected with driving reel 15, and has a slipping clutch mechanism. Winding reel 21 that constitutes the winding mechanism for holding film 7 is provided so as to be connected with driving reel 20, and has a slipping clutch mechanism.

Figure 5:
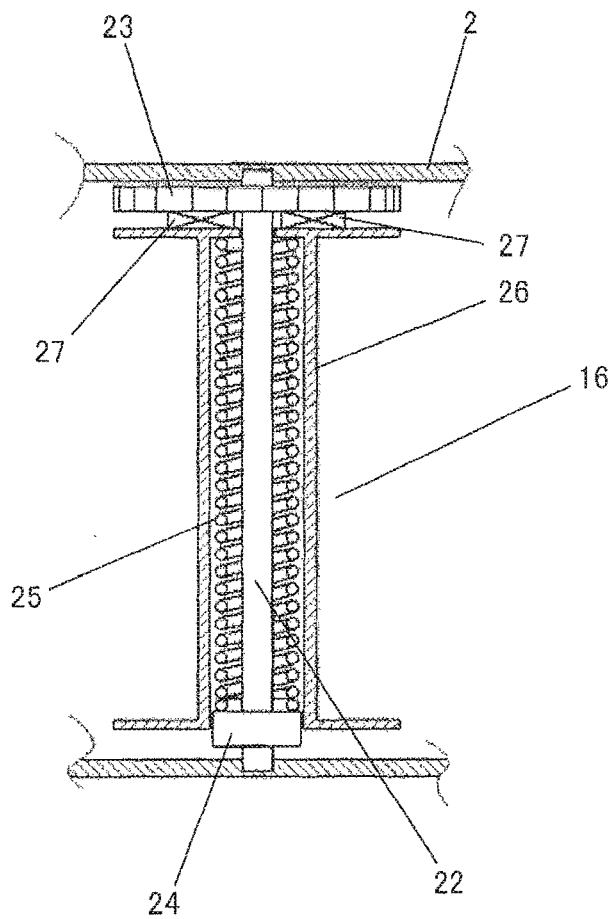
FIG. 5 is a cross-sectional diagram of the principal part of a winding reel constituting a winding mechanism of the biological information detection sensor feeding apparatus according to Embodiment 1.

The clutch mechanisms of winding reels 16, 21 are general slipping clutch mechanisms, and therefore, detailed descriptions thereof are omitted and an example thereof is shown in FIG. 5. Winding reel 16 shown in FIG. 5 has reel spindle 22. Gear 23 is provided at one end of reel spindle 22, and spring retainer 24 is provided at the other end. Around reel spindle 22, coil spring 25 is attached in a compression state.

Furthermore, around reel spindle 22, reeling part 26 is attached through coil spring 25. By coil spring 25, the gear 23 side end of reeling part 26 is pressed onto gear 23 through slipping member 27 composed of felt. When winding load with a predetermined value or more is applied to reeling part 26, reeling part 26 slips on slipping member 27 and winding reel 16 runs idle.

Winding reel 16 is connected with driving reel 15 by gear 23 (see FIG. 3A), and winding reel 16 is configured to rotate 1.2 cycles when driving reel 15 rotates 1 cycle. Thereby, the rotation amount of winding reel 16 is more than the rotation amount of driving reel 15. However, since the slipping clutch mechanism of winding reel 16 allows winding reel 16 to appropriately run idle, winding reel 16 can appropriately wind covering film 8 to which an appropriate tension is given.

Winding reel 21 to wind holding film 7 can be configured in the same manner as winding reel 16. Accordingly, winding reel 21 can appropriately wind holding film 7 to which an appropriate tension is given.

Operating lever 5 is connected with driving reel 20 and driving reel 15 through a ratchet mechanism. In FIG. 1, only when operating lever 5 is pulled up rearward, driving reel 20 and driving reel 15 rotate in predetermined directions. The rotation amounts of driving reel 20 and driving reel 15 are set so as to correspond to the operation amount of operating lever 5.

The operation of biological information detection sensor feeding apparatus 1 having the above configuration in use will be described hereinafter. First, in FIG. 1, a user (for example, a nurse) holds the upper surface of the front-end side of body case 2 with the right hand, for example, and pulls up operating lever 5 rearward by a predetermined amount with the left hand. Then, corresponding to the operation of operating lever 5, driving reel 20 rotates in a predetermined direction (see FIG. 3A). Similarly, driving reel 15 connected with driving reel 20 also rotates in a predetermined direction.

Driving projections 15*a* of driving reel 15 transmit driving force to covering film 8, through feed guide holes 9 of covering film 8 that engage with driving projections 15*a*. Thereby, covering film 8 is unwound from storage section 10 by a predetermined amount corresponding to the operation of operating lever 5, by the winding mechanism for covering film 8 (operating lever 5, winding reel 16, driving reel 15, guiding pulleys 14, 13, and separating pulley 12).

Driving projections 20*a* of driving reel 20 transmit driving force to holding film 7, through feed guide holes 9 of holding film 7 that engage with driving projections 20*a*. Thereby, holding film 7 is unwound from storage section 10 by a predetermined amount corresponding to the operation of operating lever 5, by the feeding section for holding film 7 (operating lever 5, winding reel 21, driving reel 20, guiding pulleys 19, 18, and returning pulley 17).

That is, covering film 8 and holding film 7, which constitute sensor feeding film 6, are unwound by the same predetermined amount, in other words, sensor feeding film 6 is fed to feeding stage 4.

When sensor feeding film 6 is fed to feeding stage 4, covering film 8 is peeled from holding film 7 by separating pulley 12 provided above guiding section 4*a*, and then is rolled upward, Cover film 8 is subsequently returned rearward, and through guiding pulleys 13, 14 and driving reel 15, is wound by winding reel 16.

Once covering film 8 is peeled from holding film 7 by separating pulley 12, blood glucose sensor 3, which has been sandwiched by holding film 7 and covering film 8, is uncovered. Then, blood glucose sensor 3 uncovered on the surface of holding film 7 is fed to feeding stage 4.

As described above, feeding stage 4 is configured such that the size thereof is greater than the size of blood glucose sensor 3. Thereby, blood glucose sensor 3 is stably held on feeding stage 4, and does not drop out of feeding stage 4.

In order to pick up blood glucose sensor 3 fed to feeding stage 4, for example, a user (a nurse) holds blood glucose sensor 3 with the pulp of forefinger F of the right hand, slides and moves blood glucose sensor 3 along feeding stage 4 (rightward in FIG. 4), and then pulls it out to the exterior of feeding stage 4 (for example, the upper side or the lower side in FIG. 4). The user pinches with the forefinger and the thumb the upper and lower sides of blood glucose sensor 3 pulled out of feeding stage 4 in this way. Thus, blood glucose sensor 3 can be stably picked up from feeding stage 4.

Particularly in the embodiment, as shown in FIG. 3B, preferably feeding stage 4 has inclining portion 4*b* that inclines downward along the feeding direction of sensor feeding film 6. With inclining portion 4*b*, the returning pulley 17 side end of feeding stage 4 is disposed below the upper end of returning pulley 17. That is, the upper end of returning pulley 17 protrudes above the returning pulley 17 side end of feeding stage 4.

As shown in FIG. 3B, inclining portion 4*b* gradually inclines downward along the feeding direction of sensor feeding film 6 (as going to returning pulley 17); the inclination angle of inclining portion 4*b* is not particularly limited. It is desirable that the inclination angle of inclining portion 4*b* be determined such that blood glucose sensor 3 can be easily taken out, in consideration of the largeness of feeding stage 4, the length of inclining portion 4*b*, the size of the finger, the diameter length of returning pulley 17 and the like.

Thereby, the user can more stably pick up blood glucose sensor 3 fed to feeding stage 4, compared to the case where feeding stage 4 does not have inclining portion 4*b*. That is, in order to pick up blood glucose sensor 3 from feeding stage 4 having inclining portion 4*b*, for example, the user holds the upper surface of blood glucose sensor 3 with the pulp of forefinger F of the right hand (see FIG. 3B), and then, slides and moves it downward (rightward in FIG. 4) along inclining portion 4*b* of feeding stage 4. Since feeding stage 4 has inclining portion 4*b*, blood glucose sensor 3 on the upper surface of feeding stage 4 is easily slid. In addition, it is possible to allow the longitudinal side end of blood glucose sensor 3 to abut against returning pulley 17 protruding above feeding stage 4. Since the whole of the longitudinal side end of blood glucose sensor 3 is allowed to abut against returning pulley 17, blood glucose sensor 3 can stably abut against returning pulley 17.

Thereafter, the user can pull out blood glucose sensor 3 to the exterior of feeding stage 4 (for example, the upper side or the lower side in FIG. 4) along returning pulley 17. By pinching the upper and lower sides of this pulled-out blood glucose sensor 3 with the forefinger and the thumb, it is possible to pick up blood glucose sensor 3 more steadily from the feeding stage.

Furthermore, since feeding stage 4 has inclining portion 4*b*, it is possible to utilize returning pulley 17 constituting the feeding stage for drop prevention of blood glucose sensor 3, and to achieve a simplification of a configuration for drop prevention. As a result, blood glucose sensor 3 is not dropped, and it is possible to increase ease of use.

Furthermore, as described above, in the embodiment, simply by pulling up operating lever 5, blood glucose sensor 3 can be fed to feeding stage 4 one by one. As shown in FIG. 4, on the surface of holding film 7 fed to feeding stage 4, the discrimination information of blood glucose sensor 3 is printed in the vicinity of blood glucose sensor 3 allowing the user to confirm (e.g., by visually) the identity of blood glucose sensor 3. The discrimination information is, for example, the holding number (the number information of blood glucose sensor 3) that shows the holding order of blood glucose sensor 3. The holding number is printed for each blood glucose sensor 3, in the descending order (for example, from 200 to 1) or in the ascending order (for example, from 1 to 200).

The nurse thus checks the holding number by visual observation when picking up blood glucose sensor 3 from feeding stage 4, and thereby confirms the number of blood glucose sensors 3 remaining in the apparatus, thus facilitating the use of apparatus.

The discrimination information printed in the vicinity of blood glucose sensor 3 is not limited to the above holding number; the discrimination information may be a code that shows the model, production lot number, usable period, destination and other information of blood glucose sensor 3. Thereby, it is possible to increase safety in work for the blood test.

In FIG. 4 and other drawings, a rotary lever is exemplified as operating lever 5, but operating lever 5 is not limited to a rotary lever, and may be a rotating operating lever with a handle, a sliding operating lever, or an operating button for electric operation.

Embodiment 2

Figure 6:
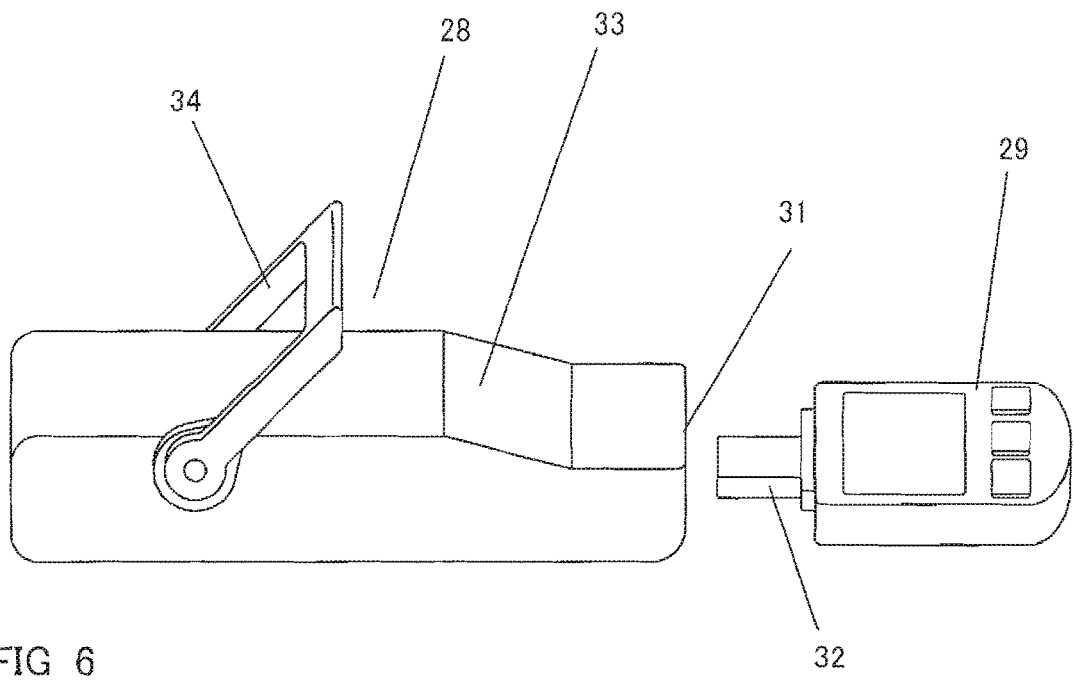
FIG. 6 is a perspective diagram of a biological information detection sensor feeding apparatus according to Embodiment 2.

FIG. 6 shows biological information detection sensor feeding apparatus 28 according to Embodiment 2. Biological information detection sensor feeding apparatus 28 feeds blood glucose sensor 30 (an example of a biological information detection sensor) shown in FIG. 7, to measurer 29 that measures biological information (for example, blood glucose level). Specifically, once cubic sensor loading section 32 provided at the end of measurer 29 is attached (inserted) to sensor feeding opening 31 (FIG. 8) provided at the front-end of biological information detection sensor feeding apparatus 28, one blood glucose sensor 30 is loaded into sensor loading section 32. The "loaded" means that blood glucose sensor 30 is electrically connected to an electric circuit of measurer 29.

Figure 8:
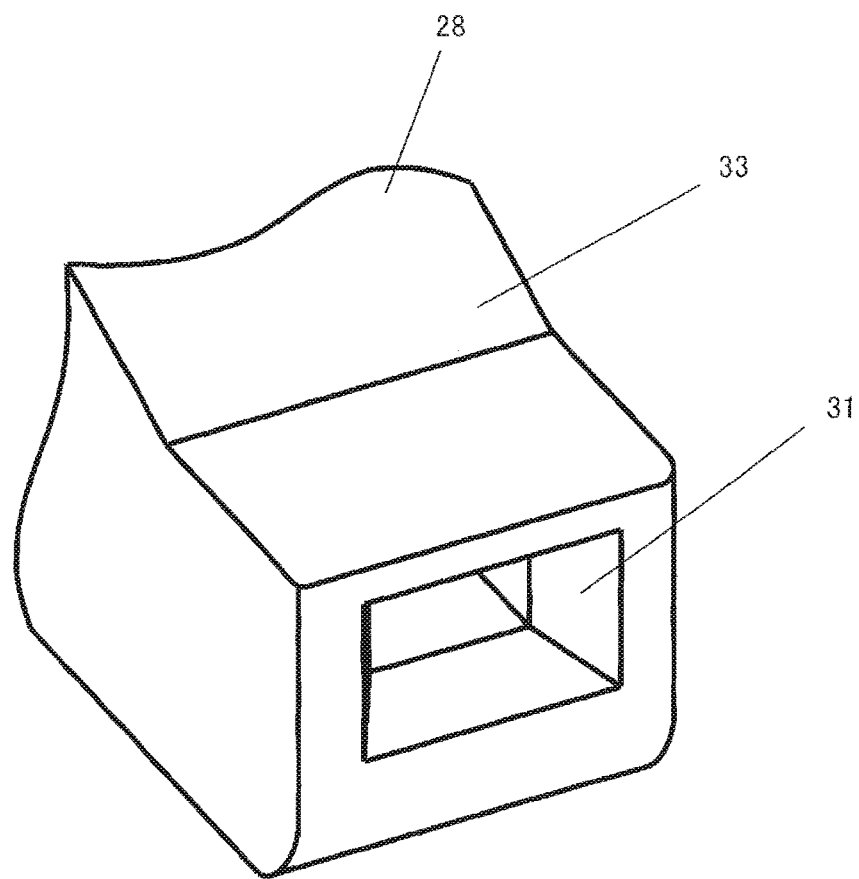
FIG. 8 is an enlarged diagram of the principal part of a feeding opening of the biological information detection sensor feeding apparatus according to Embodiment 2.
Figure 9:
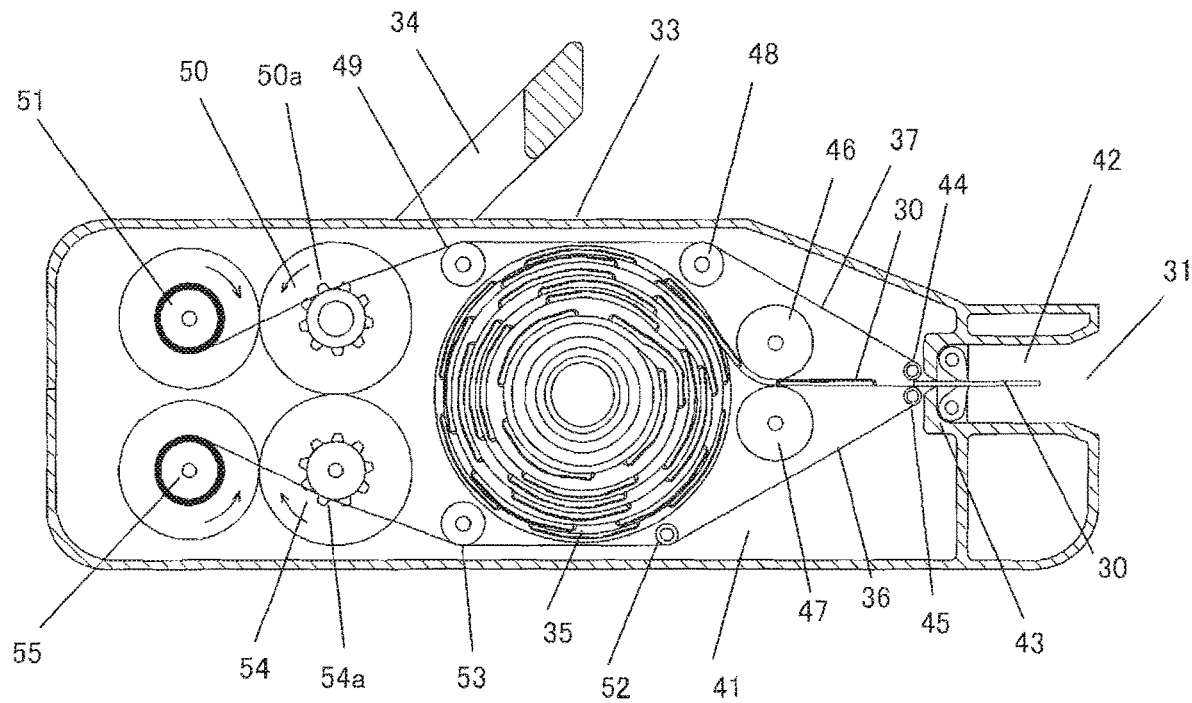
FIG. 9 is a lateral cross-sectional diagram of the biological information detection sensor feeding apparatus according to Embodiment 2.

Biological information detection sensor feeding apparatus 28 has approximately cuboidal body case 33. As shown in FIG. 8 and FIG. 9, at the front-end side of body case 33, there is provided feeding opening 31 to which blood glucose sensor 30 (an example of a biological information detection sensor) is fed.

As shown in FIG. 6, at the rear side of body case 33, there is provided operating lever 34 for feeding blood glucose sensor 30 to feeding opening 31 one by one.

Figure 7:
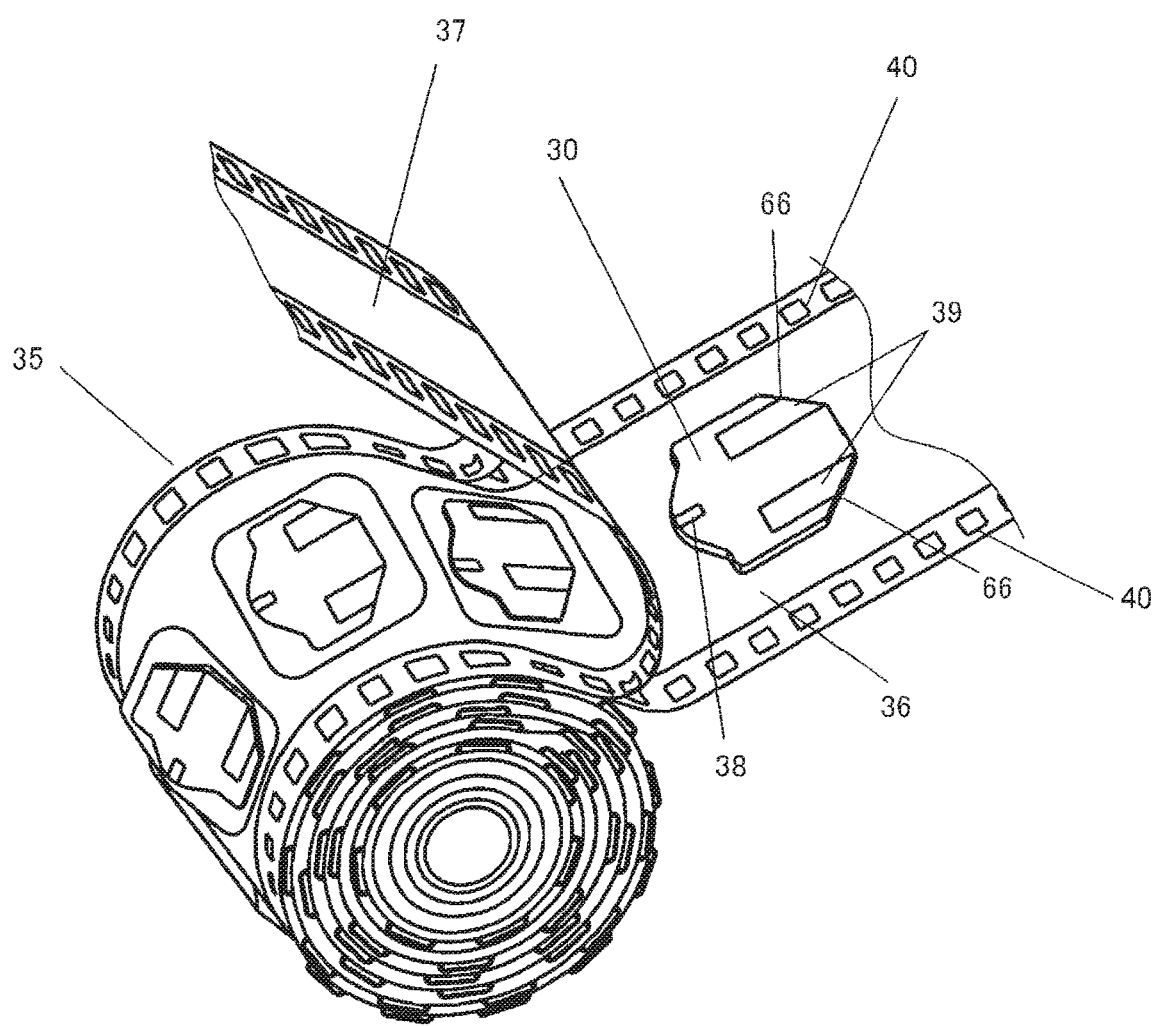
FIG. 7 is a perspective diagram of a sensor feeding film of the biological information detection sensor feeding apparatus according to Embodiment 2.

As shown in FIG. 7, blood glucose sensor 30 is stored in strip-shaped sensor feeding film 35. Sensor feeding film 35 is constituted by strip-shaped holding film 36 and strip-shaped covering film 37 that covers a surface of holding film 36.

Blood glucose sensor 30 is stored between strip-shaped holding film 36 and strip-shaped covering film 37. That is, on the surface of holding film 36, multiple (in the embodiment, 200 blood glucose sensors 30 are arranged at a predetermined interval along the longitudinal direction of holding film 36. Thus, blood glucose sensor 30 is held while being sandwiched between holding film 36 and covering film 37.

Blood glucose sensor 30 has a thin-plate shape. Spot-application portion 38 on which blood is to be spot-applied is provided on a protruding portion provided at one end, and connecting electrodes 39 are provided from the center portion to the other side end.

Feed guide holes 40 are provided at both ends in the direction orthogonal to the longitudinal direction of sensor feeding film 35. Through feed guide holes 40, driving force is transmitted to sensor feeding film 35, and a predetermined length of sensor feeding film 35 is fed toward feeding opening 31 of body case 33.

Figure 10:
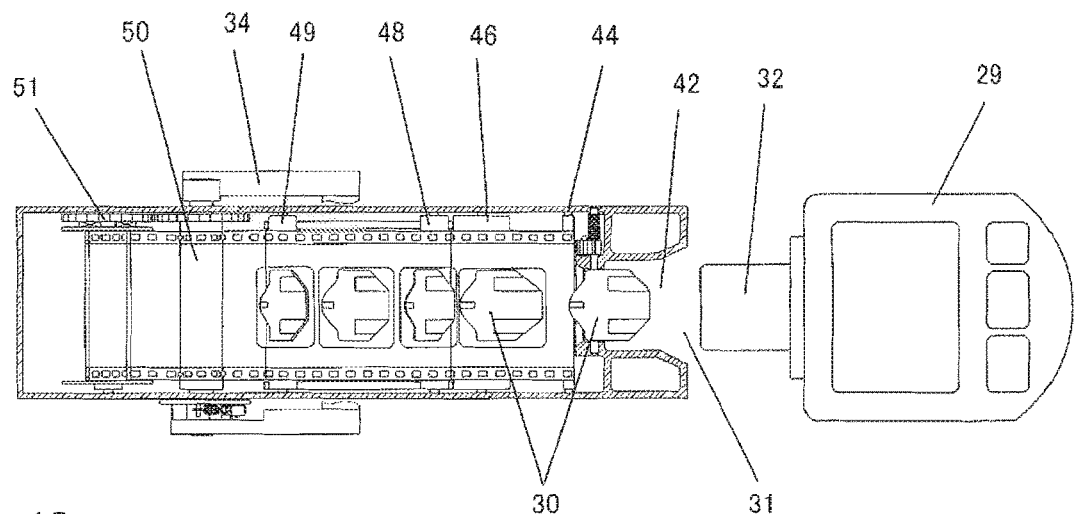
FIG. 10 is a perspective top diagram of the biological information detection sensor feeding apparatus according to Embodiment 2.

FIG. 9 is a cross-sectional diagram of biological information detection sensor feeding apparatus 28 when body case 33 is viewed in the lateral direction. FIG. 10 is a perspective diagram of biological information detection sensor feeding apparatus 28 when body case 33 is viewed in the overhead direction. For description of the internal mechanism, FIG. 10 shows a state in which the upper surface of body case 33 is removed.

As shown in FIG. 9, a roll of sensor feeding film 35 is stored in storage section 41 of body case 33. Storage section 41 only has to be provided near the center of the interior of body case 33. Sensor feeding film 35 is loosely wound so that blood glucose sensor 30 stored therein is not damaged.

As shown in FIG. 9 and FIG. 10, the roll of sensor feeding film 35 is disposed such that the unwinding direction of sensor feeding film 35 is oriented to feeding opening 31 provided at the front-end side of body case 33. As shown in FIG. 9, sensor feeding film 35, in which from the bottom in the drawing, holding film 36, blood glucose sensor 30 and covering film 37 are sequentially laminated, is fed toward feeding opening 31. Blood glucose sensor 30 is held on holding film 36 such that connecting electrodes 39 of blood glucose sensor 30 fed to sensor feeding opening 31 opposes sensor loading section 32.

As shown in FIG. 9, body case 33 of biological information detection sensor feeding apparatus 28 according to the embodiment has cuboidal sensor feeding space 42 that allows feeding opening 31 and the interior of body case 33 to communicate with each other.

Sensor holding section 43 is provided at the inward side (the leftward side in FIG. 9, the side opposite to feeding opening 31) of sensor feeding space 42. Through sensor holding section 43, blood glucose sensor 30 is fed to sensor feeding space 42.

The length from sensor holding section 43 to feeding opening 31 of sensor feeding space 42 is greater than the length of blood glucose sensor 30 (the length from the end of the spot-application portion 38 side to the end of the connecting electrode 39 side). Thereby, the whole of blood glucose sensor 30 held by sensor holding section 43 fits within sensor feeding space 42, and it does not protrude from feeding opening 31 of body case 33. Therefore, blood glucose sensor 30 is not subject to a touch by a user (a nurse).

Figure 11:
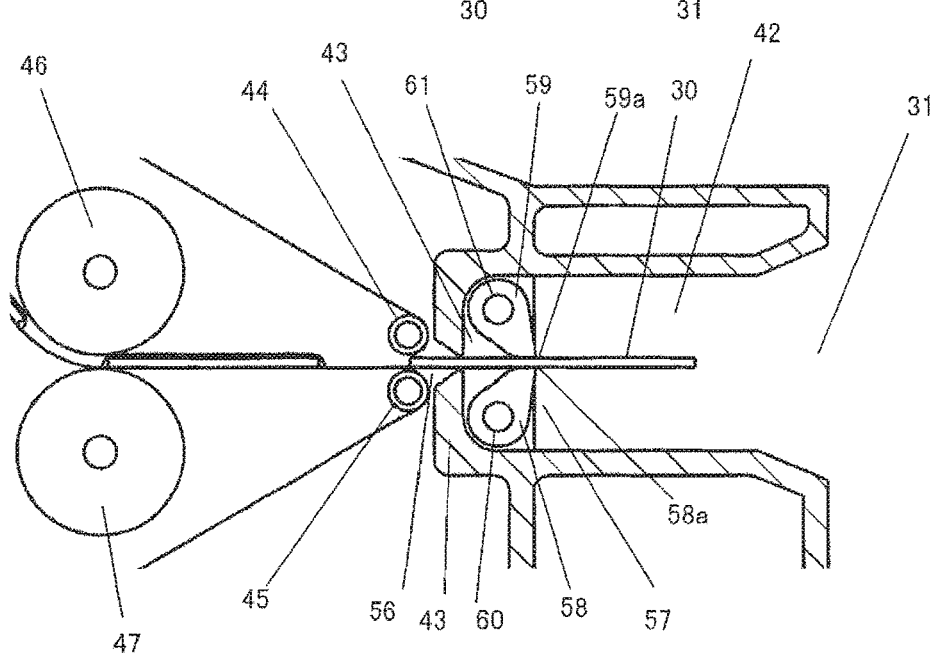
FIG. 11 is a lateral cross-sectional diagram of the principal part in the vicinity of the feeding opening of the biological information detection sensor feeding apparatus according to Embodiment 2.

As shown in FIG. 9 to FIG. 11, the vicinity of feeding opening 31 in sensor feeding space 42 has a taper shape, and the opening area of sensor feeding space 42 becomes larger outward. Thereby, the sensor loading section 32 (see FIG. 6) of measurer 29 is easily inserted to sensor feeding space 42.

In the inside of body case 33, cylindrical separating pulleys 44, 45 are provided at a region opposite to sensor holding section 43. Furthermore, a pair of cylindrical pressing pulleys 46, 47 is disposed at the inward side (storage section 41 side) of separating pulleys 44, 45. Pressing pulleys 46, 47 have a length that is greater than the short-directional width of sensor feeding film 35, and press the whole of the short-directional width of sensor feeding film 35. Pressing pulleys 46, 47 correct peculiar windings remaining in unwound sensor feeding film 35, and send it to the gap between separating pulleys 44, 45.

Separating pulleys 44, 45 separate sensor feeding film 35 into covering film 37 and holding film 36.

Separating pulley 44 returns covering film 37 of sensor feeding film 35 upward and subsequently rearward. Covering film 37 is wound by cylindrical winding reel 51, through cylindrical guiding pulleys 48, 49 and cylindrical driving reel 50. As understood from FIG. 10, the axial lengths of separating pulley 44, guiding pulleys 48, 49 and driving reel 50 are greater than the short-directional width of sensor feeding film 35.

On the other hand, separating pulley 45 returns holding film 36 of sensor feeding film 35 downward and subsequently rearward. Holding film 36 is wound by cylindrical winding reel 55, through cylindrical guiding pulleys 52, 53 and cylindrical driving reel 54. The axial lengths of separating pulley 45, guiding pulleys 52, 53 and driving reel 54 are greater than the short-directional width of sensor feeding film 35.

Driving projections 50a, 54a are provided at both end sides of driving reels 50, 54. Driving projections 50a, 54a engage with feed guide holes 40 provided at both ends of sensor feeding film 35. Driving reels 50, 54 are coupled with operating lever 34.

That is, a winding mechanism for covering film 37 of sensor feeding film 35 is constituted by operating lever 34, winding reel 51, driving reel 50, guiding pulleys 49, 48 and separating pulley 44.

A winding mechanism for holding film 36 of sensor feeding film 35 is constituted by operating lever 34, winding reel 55, driving reel 54, guiding pulleys 53, 52 and separating pulley 45.

Winding reel 51 has the same slipping clutch mechanism as Embodiment 1, and is connected with driving reel 50. Winding reel 55 has the same slipping clutch mechanism as Embodiment 1, and is connected with driving reel 54.

Operating lever 34 is connected with driving reel 50 and driving reel 54 through a ratchet mechanism. Driving reel 50 and driving reel 54 rotate in predetermined directions, only when operating lever 34 is pulled up rearward (see FIG. 6). The rotation amounts of driving reel 50 and driving reel 54 correspond to the operation of operating lever 34.

The operation of biological information detection sensor feeding apparatus 28 having the above configuration in use will be described hereinafter. First, a user (a nurse), for example, holds the upper surface of the front-end side of body case 33 with the right hand, and pulls up operating lever 34 rearward by a predetermined amount with the left hand (see FIG. 6). Then, driving reel 50 and driving reel 54 rotate in predetermined directions by the amounts corresponding to the operation of operating lever 34 (see FIG. 9).

Driving projections 50a of driving reel 50 transmit driving force to covering film 37 through feed guide holes 40 of covering film 37. As a result, covering film 37 is pulled out from storage section 41 to feeding opening 31 side by a predetermined amount corresponding to the operation of operating lever 34, by the winding mechanism for covering film 37 (operating lever 34, winding reel 51, driving reel 50, guiding pulleys 49, 48, and separating pulley 44).

Driving projections 54a of driving reel 54 transmit driving force to holding film 36 through feed guide holes 40 of holding film 36. As a result, holding film 36 is pulled out from storage section 41 to feeding opening 31 side by a predetermined amount corresponding to the operation of operating lever 34, by the winding mechanism for holding film 36 (operating lever 34, driving reel 54, guiding pulleys 53, 52, separating pulley 45, and winding reel 55).

That is, covering film 37 and holding film 36 are pulled out to feeding opening 31 side by the same predetermined amount. In other words, sensor feeding film 35 is pulled out. Covering film 37 and holding film 36 are separated from pulled-out sensor feeding film 35 by separating pulleys 44, 45. Then, one blood glucose sensor 30 stored in sensor feeding film 35 is fed to sensor feeding space 42.

FIG. 11 shows a state in which one blood glucose sensor 30 has been fed to sensor feeding space 42. FIG. 11 is an enlarged cross-sectional diagram of the vicinity of feeding opening 31. In the embodiment, blood glucose sensor 30 fed to sensor feeding space 42 can be stably held by sensor holding section 43. To describe more specifically, sensor holding section 43 has guiding opening 56 that is opened in an oblong shape. Guiding opening 56 is formed in a taper shape, in order to easily guide blood glucose sensor 30 to feeding opening 31 side. In order that blood glucose sensor 30 can be sandwiched and held at the opening portion on feeding opening 31 side in guiding opening 56, the gap of the opening portion is nearly equal to, or slightly greater than the thickness of blood glucose sensor 30. At feeding opening 31 side of guiding opening 56, there is provided sandwiching section 57, which sandwiches blood glucose sensor 30 that has been guided to guiding opening 56 and moved to feeding opening 31 side. That is, sensor holding section 43 is constituted by guiding opening 56 and sandwiching section 57.

In guiding opening 56, the opening area of the inward side (the leftward side in FIG. 11, the side from guiding opening 56 to separating pulleys 44, 45) of body case 33 is greater than the opening area of the outward side (the rightward side in FIG. 11, the side from guiding opening 56 to feeding opening 31) of body case 33. Thereby, blood glucose sensor 30 to be fed can be securely led to the interior of guiding opening 56, and furthermore, can be appropriately guided to sandwiching section 57.

Figure 12:
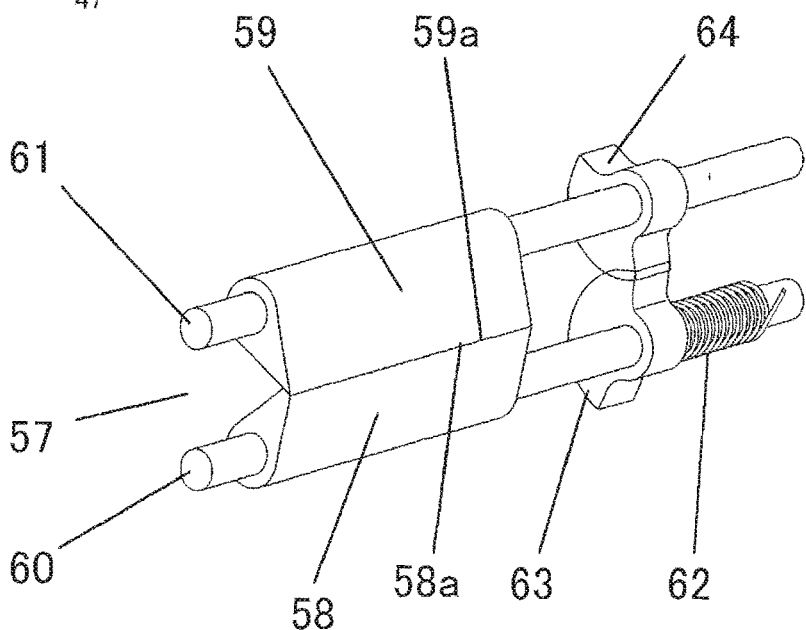
FIG. 12 is a perspective diagram of the principal part of the feeding opening of the biological information detection sensor feeding apparatus according to Embodiment 2.
Figure 13:
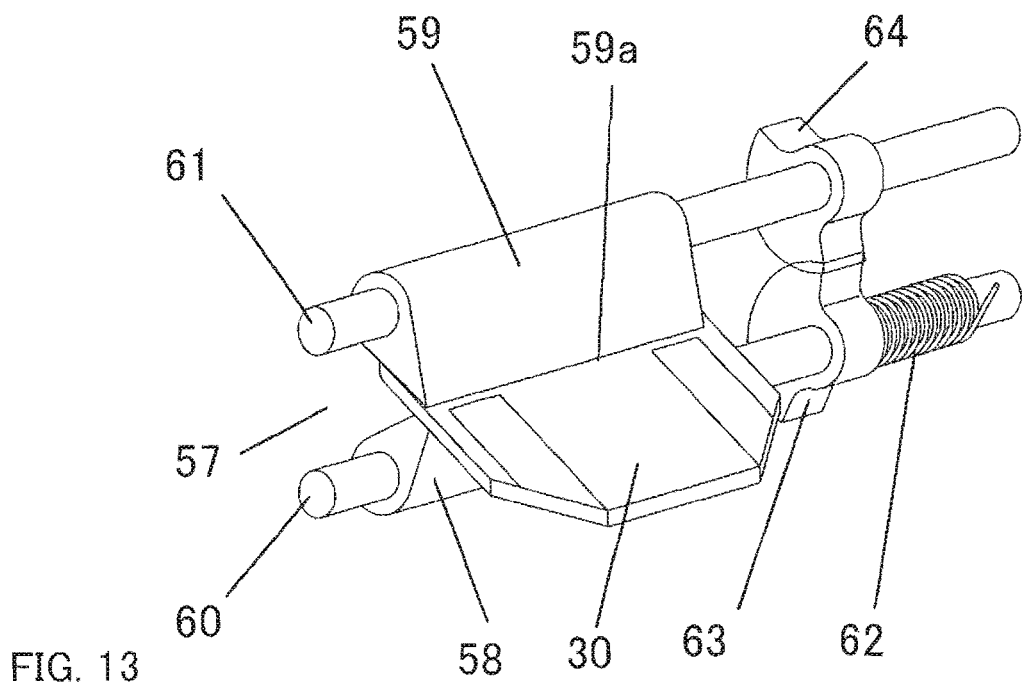
FIG. 13 is a perspective diagram of the principal part of the feeding opening of the biological information detection sensor feeding apparatus according to Embodiment 2.

FIG. 12 and FIG. 13 are enlarged perspective diagrams of sandwiching section 57, viewed from feeding opening 31 side. As shown in FIG. 12 and FIG. 13, sandwiching section 57 has oblong sandwiching claws 58, 59 opposite to each other, which are disposed such that the opposing portion between sandwiching claws 58, 59 is parallel to the long axis of guiding opening 56 (see FIG. 11). The opposing portion between sandwiching claws 58, 59 corresponds to abutting portions 58a, 59a that abut against blood glucose sensor 30. As shown in FIG. 13, abutting portions 58a, 59a are configured to sandwich the top and bottom surfaces of blood glucose sensor 30.

Sandwiching section 57 has rotating shafts 60, 61 that rotate sandwiching claws 58, 59. As shown in FIG. 11, abutting portions 58a, 59a are disposed closer to feeding opening 31 than rotating shafts 60, 61. Thereby, sandwiching section 57 sandwiches blood glucose sensor 30 at a position closer to feeding opening 31 than rotating shafts 60, 61.

As shown in FIG. 12 and FIG. 13, rotating shafts 60, 61 are equipped with rotating cams 63, 64, and rotate synchronously therewith. Thereby, abutting portions 58a, 59a of sandwiching section 57 can always sandwich blood glucose sensor 30 at the same position.

Furthermore, rotating shaft 60 includes spring 62. Thereby, spring 62, rotating cam 63 and rotating cam 64 always bias sandwiching claws 58, 59, and act to abut against abutting portions 58a, 59a.

As shown in FIG. 11, abutting portions 58a, 59a are disposed closer to feeding opening 31 than rotating shafts 60, 61. Thereby, blood glucose sensor 30, which advances from rotating shafts 60, 61 side to feeding opening 31 side (from the left side to the right side in FIG. 11), can open sandwiching claws 58, 59. That is, sandwiching claws 58, 59 do not obstruct the advance of blood glucose sensor 30.

On the other hand, if blood glucose sensor 30 tries to retract from feeding opening 31 side to rotating shafts 60, 61 side (from the right side to the left side in FIG. 11), sandwiching claws 58, 59 are pulled by blood glucose sensor 30 and try to close, so that sandwiching claws 58, 59 strongly sandwich the upper and lower surfaces of blood glucose sensor 30. Thereby, blood glucose sensor 30 does not retract from feeding opening 31 side to rotating shafts 60, 61 side (from the right side to the left side in FIG. 11).

Figure 14:
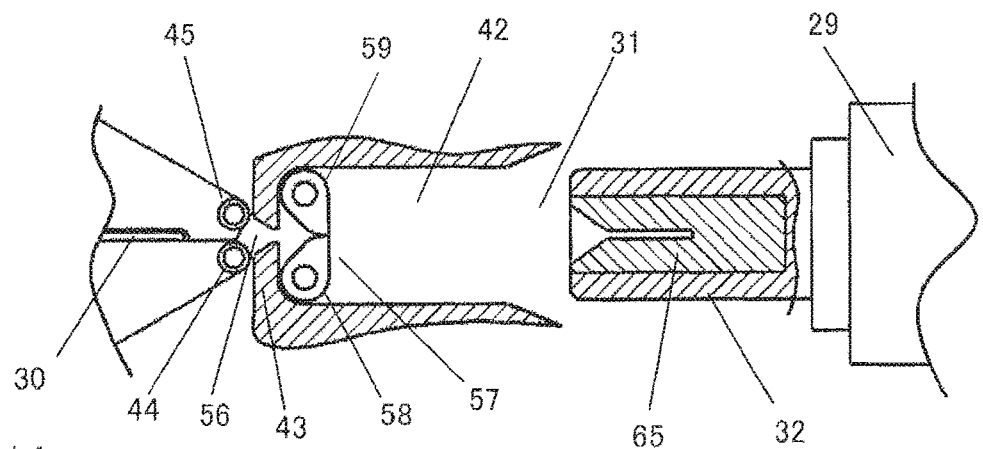
FIG. 14 is a lateral cross-sectional diagram of the principal part of the feeding opening of the biological information detection sensor feeding apparatus according to Embodiment 2.
Figure 15:
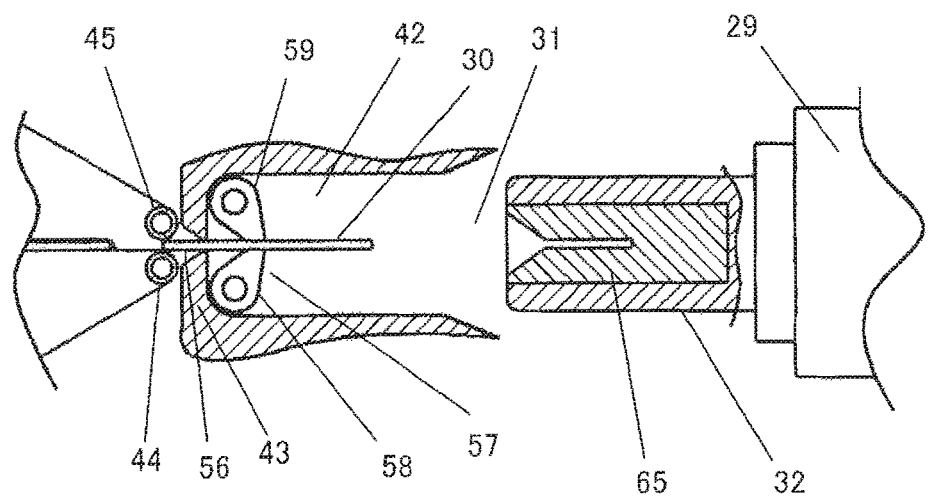
FIG. 15 is a lateral cross-sectional diagram of the principal part of the feeding opening of the biological information detection sensor feeding apparatus according to Embodiment 2.

When blood glucose sensor 30, from a state shown in FIG. 14, is guided to guiding opening 56 and is fed to sensor feeding space 42, sandwiching section 57 sandwiches the center portion of blood glucose sensor 30, as shown in FIG. 15. In addition, by the opening portion on feeding opening 31 side in guiding opening 56, blood glucose sensor 30 can be held by sandwiching. Thus, blood glucose sensor 30 can be held by the opening portion on feeding opening 31 side in guiding opening 56 while being sandwiched by sandwiching section 57. Thereby, it is possible to stably keep the position of blood glucose sensor 30 fed to sensor feeding space 42.

That is, although blood glucose sensor 30 fed to sensor feeding space 42 is not held by separating pulleys 44, 45 anymore, sandwiching section 57 sandwiches the center portion of blood glucose sensor 30, and guiding opening 56 holds one side of blood glucose sensor 30. Therefore, blood glucose sensor 30 can be stably held in sensor feeding space 42.

Figure 16:
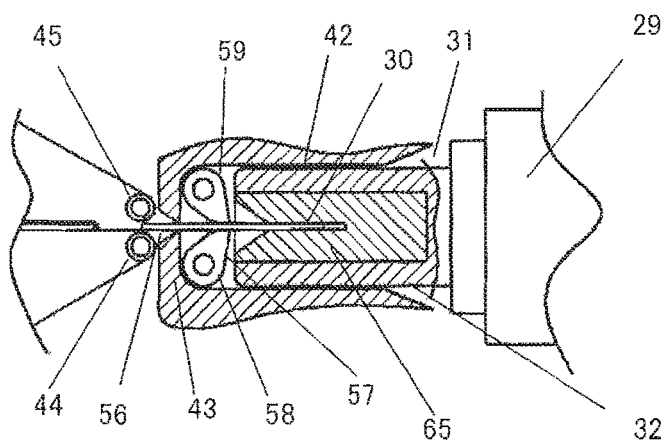
FIG. 16 is a lateral cross-sectional diagram of the principal part of the feeding opening of the biological information detection sensor feeding apparatus according to Embodiment 2.

Thereafter, as shown in FIG. 16, a user (a nurse) attaches (inserts) sensor loading section 32 (see FIG. 10) of measurer 29 from feeding opening 31 to sensor feeding space 42. Then, connecting electrodes 39 of blood glucose sensor 30 held in sensor feeding space 42 are mechanically and electrically connected to connector 65 in sensor loading section 32. When inserting sensor loading section 32 to sensor feeding space 42, sensor loading section 32 would push back blood glucose sensor 30. However, as described above, sandwiching claws 58, 59 strongly sandwiches the upper and lower surfaces of blood glucose sensor 30, and therefore blood glucose sensor 30 is not pushed back. Thereby, blood glucose sensor 30 can be appropriately connected to connector 65.

As shown in FIG. 7, blood glucose sensor 30 has guiding cutouts 66 provided by cutting out the end of the connecting electrode 39 side. By guiding cutouts 66, blood glucose sensor 30 is guided to connector 65 so that connecting electrodes 39 can be appropriately connected to connector 65.

Figure 17:
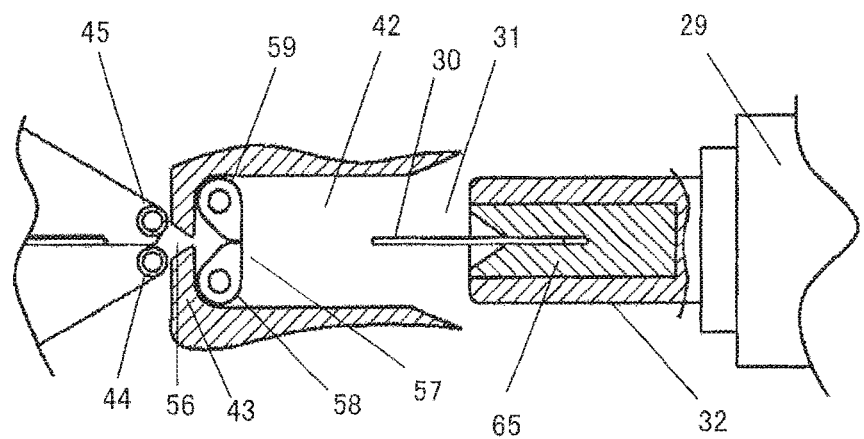
FIG. 17 is a lateral cross-sectional diagram of the principal part of the feeding opening of the biological information detection sensor feeding apparatus according to Embodiment 2.

Finally, as shown in FIG. 17, the user (nurse) pulls out sensor loading section 32 from feeding opening 31. In sensor loading section 32 of pulled-out measurer 29, blood glucose sensor 30 has been loaded.

When inserting sensor loading section 32 of measurer 29 to sensor feeding space 42, sandwiching claws 58, 59 strongly sandwiches the upper and lower surfaces of blood glucose sensor 30. Thereafter, by pulling out sensor loading section 32 of measurer 29 from sensor feeding space 42, the sandwiching between sandwiching claws 58, 59 becomes loose and blood glucose sensor 30 is released. As a result, as shown in FIG. 17, blood glucose sensor 30 is securely transferred to measurer 29.

Naturally, connector 65 of sensor loading section 32 is configured to connect with connecting electrodes 39 of blood glucose sensor 30 while being pressed thereon, when blood glucose sensor 30 is inserted to sensor loading section 32. This stabilizes the electric connecting condition between connector 65 and connecting electrodes 39, and results in a more secure loading of blood glucose sensor 30 into blood glucose sensor 30.

As described above, biological information detection sensor feeding apparatus 28 according to the embodiment has the following features.

(1) The apparatus includes body case 33 having feeding opening 31 for blood glucose sensor 30 (biological information detection sensor), storage section 41 that stores strip-shaped sensor feeding film 35 in body case 33, and the feeding section that feeds a predetermined length of sensor feeding film 35 from storage section 41 to feeding opening 31.

Sensor feeding film 35 has strip-shaped holding film 36, strip-shaped covering film 37 covering the surface of holding film 36, and multiple blood glucose sensors 30 that are sandwiched and held by holding film 36 and covering film 37.

The feeding section is configured to feed a predetermined length of sensor feeding film 35 to feeding opening 31, to separate holding film 36 and covering film 37 immediately before feeding opening 31, and to feed blood glucose sensor 30 to feeding opening 31 side.

Furthermore, in feeding opening 31, sensor holding section 43 that holds blood glucose sensor 30 is provided at the inward side of body case 33. Sensor holding section 43 includes guiding opening 56 that guides blood glucose sensor 30 to feeding opening 31 side, and sandwiching section 57 that sandwiches blood glucose sensor 30 guided by guiding opening 56 and moved to feeding opening 31 side.

(2) Sandwiching section 57 includes sandwiching claw 58 and sandwiching claw 59 that sandwich the top and bottom surfaces of blood glucose sensor 30. Sandwiching claw 58 and sandwiching claw 59 have abutting portion 58a and abutting portion 58b that abut against blood glucose sensor 30, and rotating shaft 60 and rotating shaft 61 that rotate sandwiching claw 58 and sandwiching claw 59. Abutting portion 58a and abutting portion 58b are disposed closer to feeding opening 31 than rotating shafts 60, 61.

(3) The rotating shafts of sandwiching claw 58 and sandwiching claw 59 are configured to abut against rotating cam 63 and rotating cam 64, respectively.

Thereby, in the embodiment, when taking out blood glucose sensor 30, holding film 36 and covering film 37 are separated from sensor feeding film 35, and, one new blood glucose sensor 30 is uncovered and then fed to feeding opening 31 through guiding opening 56 so as to fit within sensor feeding space 42. Then, blood glucose sensor 30 fed to feeding opening 31 is sandwiched and held by sandwiching section 57 of sensor holding section 43.

When blood glucose sensor 30 is being held by sandwiching section 57 of sensor holding section 43, once measurer 29 is attached (inserted) from feeding opening 31 to sensor feeding space 42, blood glucose sensor 30 is loaded into measurer 29.

That is, according to the embodiment, a user himself does not need to peel sensor feeding film 35 in order to take out blood glucose sensors 30 from sensor feeding film 35 one by one. In addition, according to the embodiment, it is also possible to load blood glucose sensor 30 into measurer 29 without touching blood glucose sensor 30 by hand. Thus, the embodiment makes it possible to easily load blood glucose sensor 30 into measurer 29, and therefore is easy to use.

As shown in FIG. 7 and FIG. 10, Embodiment 2 differs from the above-described Embodiment 1 in the orientation of blood glucose sensor 30 that is being stored in sensor feeding film 35. This is because a main object of Embodiment 1 is to securely and easily take out blood glucose sensor 3 with fingers or the like, whereas a main object of Embodiment 2 is to directly load blood glucose sensor 30 into loading section 32 of measurer 29.

Modification 1 of Embodiment 2

In Embodiment 2, since measurer 29 has sensor loading section 32 protruding from the housing of measurer 29, it is possible to regulate the attaching position of measurer 29 by conforming the shape of sensor loading section 32 to sensor feeding space 42. In contrast, biological information detection sensor feeding apparatus 28' according to Modification 1 of Embodiment 2 supplies biological information detection sensor 30 to measurer 29' that has sensor loading section 32' provided in the interior of the housing of the measurer, unlike sensor loading section 32 of the above-described measurer 29.

As shown in FIGS. 18 to 21, measurer 29' has displaying section 29a that displays measured values and the like, operating section 29b that is constituted by various buttons, and sensor loading section 32' into which biological information detection sensor 30 is to be loaded. Biological information detection sensor feeding apparatus 28' has the same configuration as the above-described biological information detection sensor feeding apparatus 28, and further has attachment 28a and end surface portion 28c having an end surface.

Figure 18:
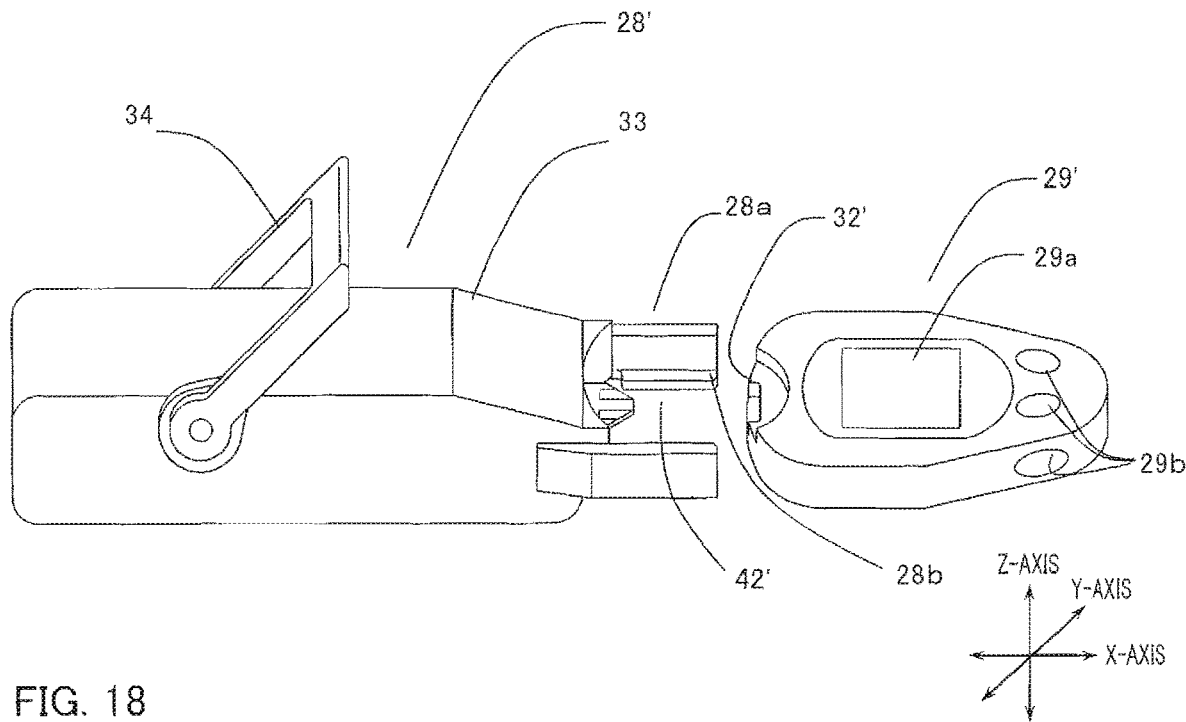
FIG. 18 is a perspective diagram of a biological information detection sensor feeding apparatus according to Modification 1 of Embodiment 2.
Figure 19:
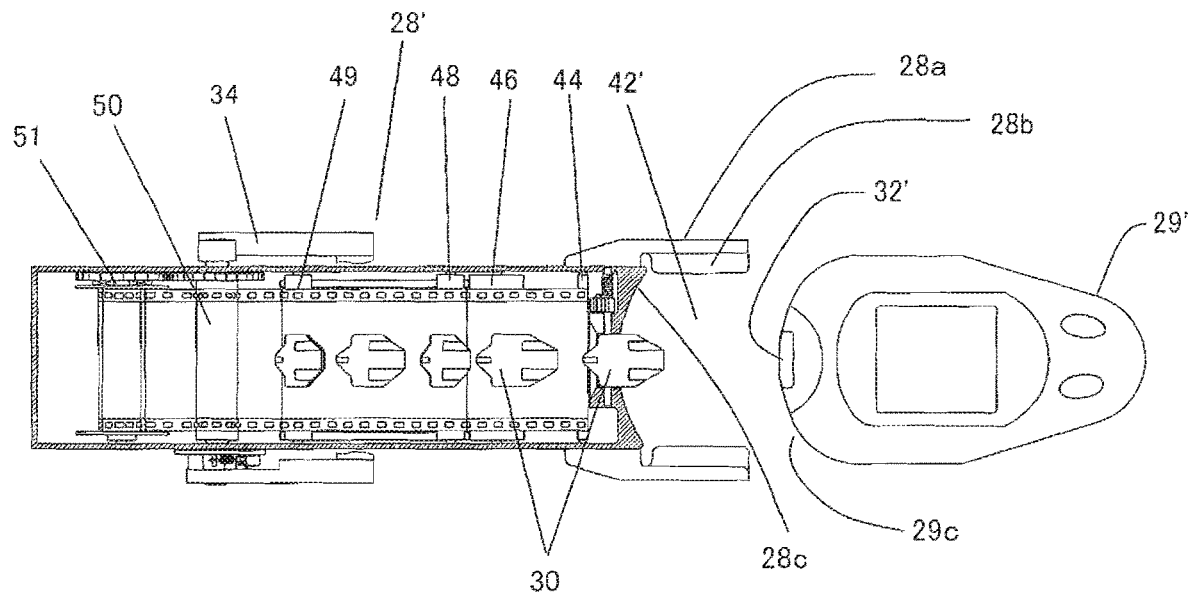
FIG. 19 is a perspective top diagram of the biological information detection sensor feeding apparatus according to Modification 1 of Embodiment 2.

As shown in FIG. 18, measurer 29' has operating section 29b. Operating section 29b, which is provided on the upper surface of measurer 29', includes a setting button by which setting data are set or selection menus are determined, a selection button by which a menu to be selected or a content to be displayed is switched, and a power button disposed on a side surface of measures 29'.

Sensor loading section 32' of measurer 29' is provided at an end of the housing of measurer 29' and that abuts against biological information detection sensor feeding apparatus 28'. Once sensor loading section 32' of measurer 29' is attached to sensor feeding space 42' that is a space for feeding blood glucose sensor 30 and is provided in biological information detection sensor feeding apparatus 28', one blood glucose sensor 30 is loaded into sensor loading section 32'.

The attaching position of measurer 29' in sensor feeding space 42' is regulated by attachment 28a of biological information detection sensor feeding apparatus 28', and the like. As shown in FIG. 18, attachment 28a defines sensor feeding space 42' of biological information detection sensor feeding apparatus 28'. Attachment 28a regulates the attaching position of measurer 29' to be attached to sensor feeding space 42', in the width direction of measurer 29', which is the direction (the Y-axis direction in FIG. 18) orthogonal to the loading direction of blood glucose sensor 30.

Attachment 28a has angle (receiving portion) 28b. Angle (receiving portion) 28b supports the lower surface and upper surface of measurer 29' to be attached to sensor feeding space 42', and thereby regulates the attaching position of measurer 29' in the direction vertical to the upper and lower surfaces of measurer 29' (the Z-axis direction in FIG. 18).

End surface portion 28c having the end surface is disposed in sensor feeding space 42' of biological information detection sensor feeding apparatus 28', close to fed blood glucose sensor 30. The end surface of end surface portion 28c has such a shape as to be abutted against case member 29c of sensor loading section 32' side of measurer 29'. By allowing the end surface of end surface portion 28c to abut against case member 29c of measurer 29', measurer 29' is regulated in the loading direction to biological information detection sensor feeding apparatus 28' (the X-axis direction in FIG. 18).

Other configurations of biological information detection sensor feeding apparatus 28' may be the same as biological information detection sensor feeding apparatus 28 according to Embodiment 2, and therefore, descriptions thereof are omitted.

The operation of biological information detection sensor feeding apparatus 28' and measurer 29' that have the above configuration in use will be described hereinafter. The operation in the feeding of blood glucose sensor 30 to sensor feeding space 42' is the same as biological information detection sensor feeding apparatus 28, and therefore, descriptions thereof are omitted (see FIG. 14, 15).

A user (a nurse) attaches sensor loading section 32' (see FIG. 19) of measurer 29' to sensor feeding space 42'. As described above, the attaching position of measurer 29' is appropriately regulated by attachment 28a, angle (receiving portion) 28b, end surface portion 28c and the like that define sensor feeding space 42' of biological information detection sensor feeding apparatus 28'. As a result, blood glucose sensor 30 is appropriately loaded into sensor loading section 32' of measurer 29'.

Figure 20:
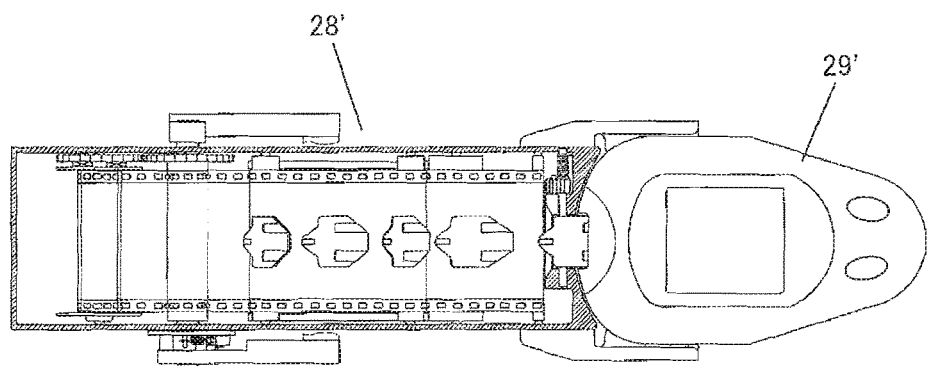
FIG. 20 is a perspective top diagram of the biological information detection sensor feeding apparatus (in a docked state) according to Modification 1 of Embodiment 2.

FIG. 20 is an overhead diagram showing a state in which case member 29c of measurer 29' abuts against biological information detection sensor feeding apparatus 28 (attached state). FIG. 20 contains a cross-sectional diagram of biological information detection sensor feeding apparatus 28' and a top diagram of measurer 29'. In FIG. 20, some reference signs are the same as in FIG. 19, and therefore are omitted.

Figure 21:
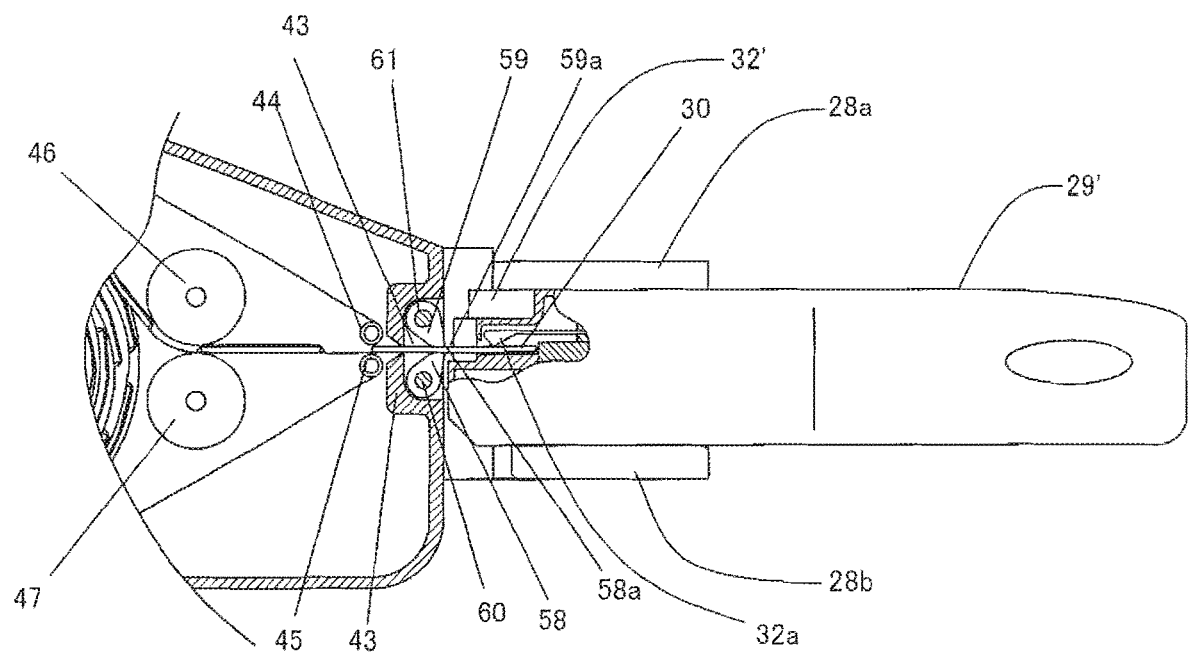
FIG. 21 is an enlarged lateral cross-sectional diagram of the principal part of the biological information detection sensor feeding apparatus (in the docked state) according to Modification 1 of Embodiment 2.

FIG. 21 is an enlarged lateral cross-sectional diagram of sensor loading section 32' and the surroundings in a state in which case member 29c of measurer 29' abuts against biological information detection sensor feeding apparatus 28' (attached state). In FIG. 21, as for measurer 29', only a region of sensor loading section 32' thereof is shown as a cross-sectional diagram.

Sensor loading section 32' has contact 32a that is a contacting terminal to blood glucose sensor 30. Blood glucose sensor 30 is loaded into sensor loading section 32' of measurer 29', and thereby, contacts with contact 32a. Thereby, blood glucose sensor 30 is electrically connected with a measuring circuit in measurer 29' through contact 32a.

As described above, the attaching position of measurer 29' is appropriately regulated by attachment 28a, angle (receiving portion) 28b, end surface portion 28c and the like that define sensor feeding space 42' of biological information detection sensor feeding apparatus 28'. Thereby, blood glucose sensor 30 is properly loaded into sensor loading section 32 of measurer 29'. That is, blood glucose sensor 30 can appropriately contact with contact 32a in sensor loading section 32'.

Thereafter, the user (nurse) pulls out measurer 29' from biological information detection sensor feeding apparatus 28'. Blood glucose sensor 30 is set apart from biological information detection sensor feeding apparatus 28', while contacting with contact 32a of sensor loading section 32'.

From the above, in Modification 1 of Embodiment 2, attachment 28a and the like that regulate measurer 29' are provided in biological information detection sensor feeding apparatus 28', and thereby, it is possible to provide biological information detection sensor feeding apparatus 28 that securely loads blood glucose sensor 30 into measurer 29' having sensor loading section 32' that is provided in the interior of the housing of measurer 29'.

Modification 2 of Embodiment 2

In biological information detection sensor feeding apparatus 28' according to Modification 1 of Embodiment 2, the attaching position of measurer 29' is regulated by attachment 28a, angle (receiving portion) 28b and end surface portion 28c. On the other hand, in biological information detection sensor feeding apparatus 28" according to Modification 2 of Embodiment 2, the attaching position of measurer 29' is regulated by end surface portion 28c and lower-surface receiving portion 28d (see FIG. 23 and FIG. 24).

Figure 22:
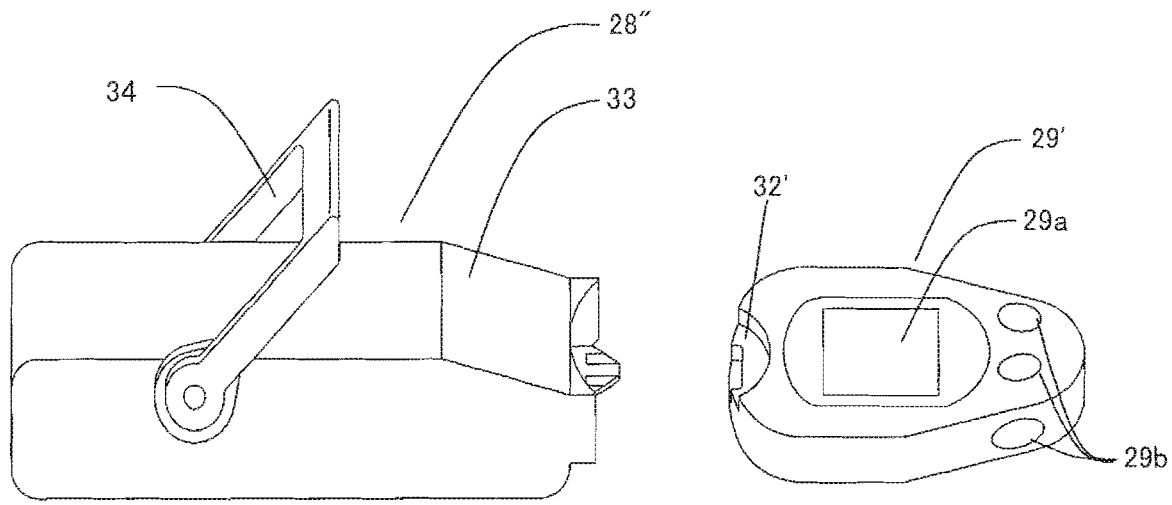
FIG. 22 is a perspective diagram of a biological information detection sensor feeding apparatus according to Modification 2 of Embodiment 2.
Figure 23:
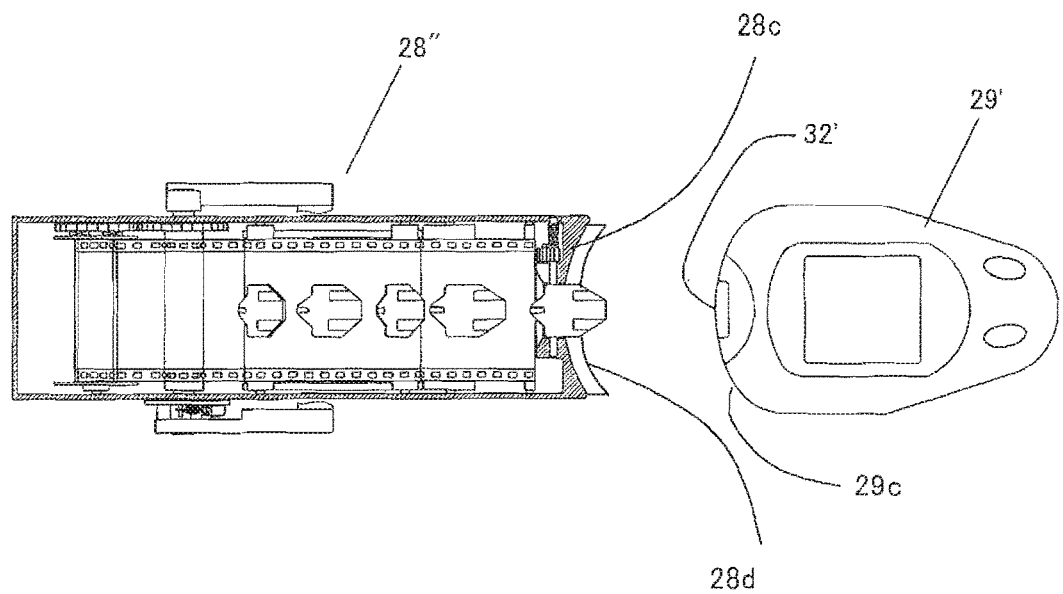
FIG. 23 is a perspective top diagram of the biological information detection sensor feeding apparatus according to Modification 2 of Embodiment 2.
Figure 24:
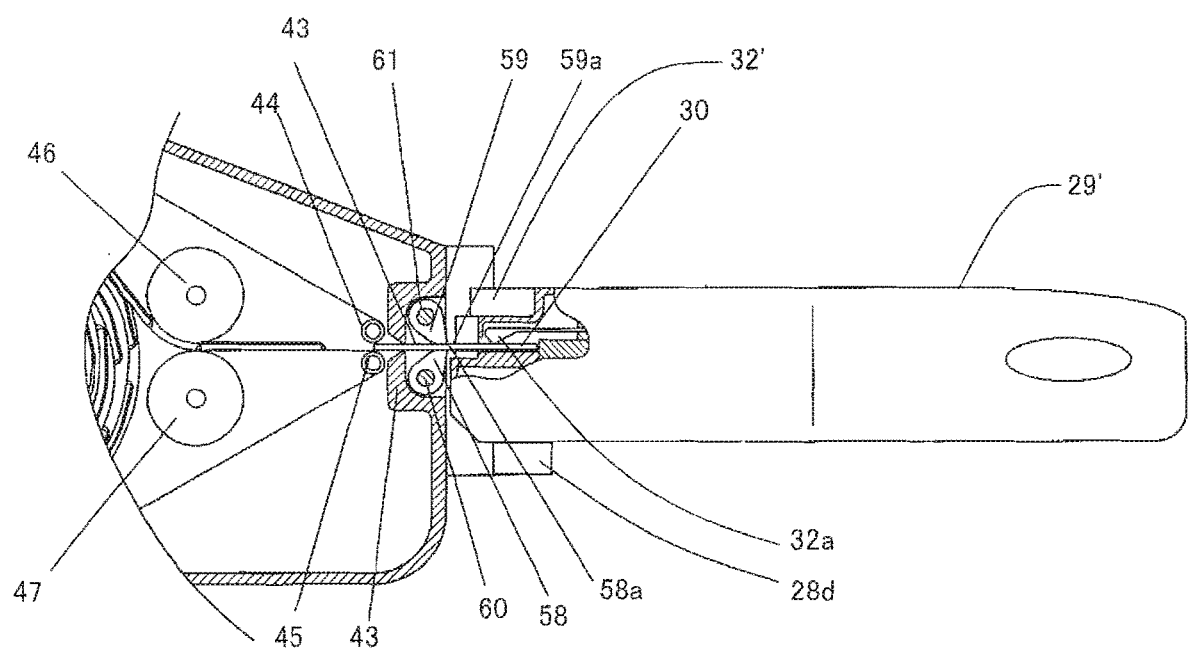
FIG. 24 is an enlarged lateral cross-sectional diagram of the principal part of the biological information detection sensor feeding apparatus (in the docked state) according to Modification 2 of Embodiment 2.

As shown in FIGS. 22 to 24, biological information detection sensor feeding apparatus 28" according to Modification 2 of Embodiment 2, which has end surface portion 28c having an end surface similarly to the above-described biological information detection sensor feeding apparatus 28' according to Modification 1 of Embodiment 2, but does not have attachment 28a in the above-described Modification 1 and has lower-surface receiving portion 28d instead. Other configurations of biological information detection sensor feeding apparatus 28" are the same as the above-described biological information detection sensor feeding apparatus 28', and therefore, descriptions thereof are omitted. On the other hand, measurer 29' according to Modification 2 of Embodiment 2 has the same configuration as measurer 29' according to Modification 1 of Embodiment 2.

In biological information detection sensor feeding apparatus 28", the attaching position of measurer 29' is regulated by end surface portion 28c having an end surface, lower-surface receiving portion 28d and the like. To take FIG. 22 as an example, end surface portion 28c has an end surface that abuts against case member 29c of measurer 29', and is disposed close to fed blood glucose sensor 30. Since the end surface of end surface portion 28c abuts against case member 29c of measurer 29', it is possible to regulate measurer 29' in the loading direction of measurer 29'. Here, end surface portion 28c has a curved concave end surface, and case member 29c has a convex end surface. In order that the concave end surface of end surface portion 28c and the convex end surface of case member 29c appropriately abut against each other, their shape is curved in a similar manner. The abutment between the concave end surface of end surface portion 28c and the convex end surface of case member 29c allows for the regulation also in the width direction of measurer 29', which is the direction orthogonal to the loading direction of blood glucose sensor 30. However, the regulation performance is less powerful than that of attachment 28a of biological information detection sensor feeding apparatus 28' according to Modification 1 of Embodiment 2.

Lower-surface receiving portion 28d supports the lower surface of measurer 29' to be attached. Lower-surface receiving portion 28d is provided at a lower portion of end surface portion 28c. Thereby, lower-surface receiving portion 28d can regulate the attaching position of measurer 29' in the vertical direction of measurer 29'.

FIG. 24 is an enlarged lateral cross-sectional diagram of sensor loading section 32' and the surroundings in a state in which the end surface of case member 29c of measurer 29' abuts against the end surface of end surface portion 28c of biological information detection sensor feeding apparatus 28" according to Modification 2 of Embodiment 2 (attached state). In FIG. 24, as for measurer 29', only a region of sensor loading section 32' is shown as a cross-sectional diagram.

Sensor loading section 32 has contact 32a that is a contacting terminal to blood glucose sensor 30. Blood glucose sensor 30 is loaded into sensor loading section 32' of measurer 29', and thereby, contacts with contact 32a. Thereby, blood glucose sensor 30 is electrically connected with a measuring circuit in measurer 29' through contact 32a.

As described above, the attaching position of measurer 29' is appropriately regulated by end surface portion 28c and lower-surface receiving portion 28d. Thereby, blood glucose sensor 30 is appropriately loaded into sensor loading section 32' of measurer 29'. That is, blood glucose sensor 30 can securely contact with contact 32a in sensor loading section 32'.

Thereafter, a user (a nurse) pulls out measurer 29' from biological information detection sensor feeding apparatus 28". Blood glucose sensor 30 is set apart from biological information detection sensor feeding apparatus 28", while contacting with contact 32a of sensor loading section 32'.

Biological information detection sensor feeding apparatus 28" according to Modification 2 of Embodiment 2 does not have attachment 28a. Thereby, biological information detection sensor feeding apparatus 28" has a simple configuration and can be downsized. Therefore, biological information detection sensor feeding apparatus 28" according to Modification 2 of Embodiment 2 makes it possible to improve the portability, while maintaining the convenience in biological information detection sensor feeding apparatuses 28, 28'.

Embodiment 3

Figure 25:
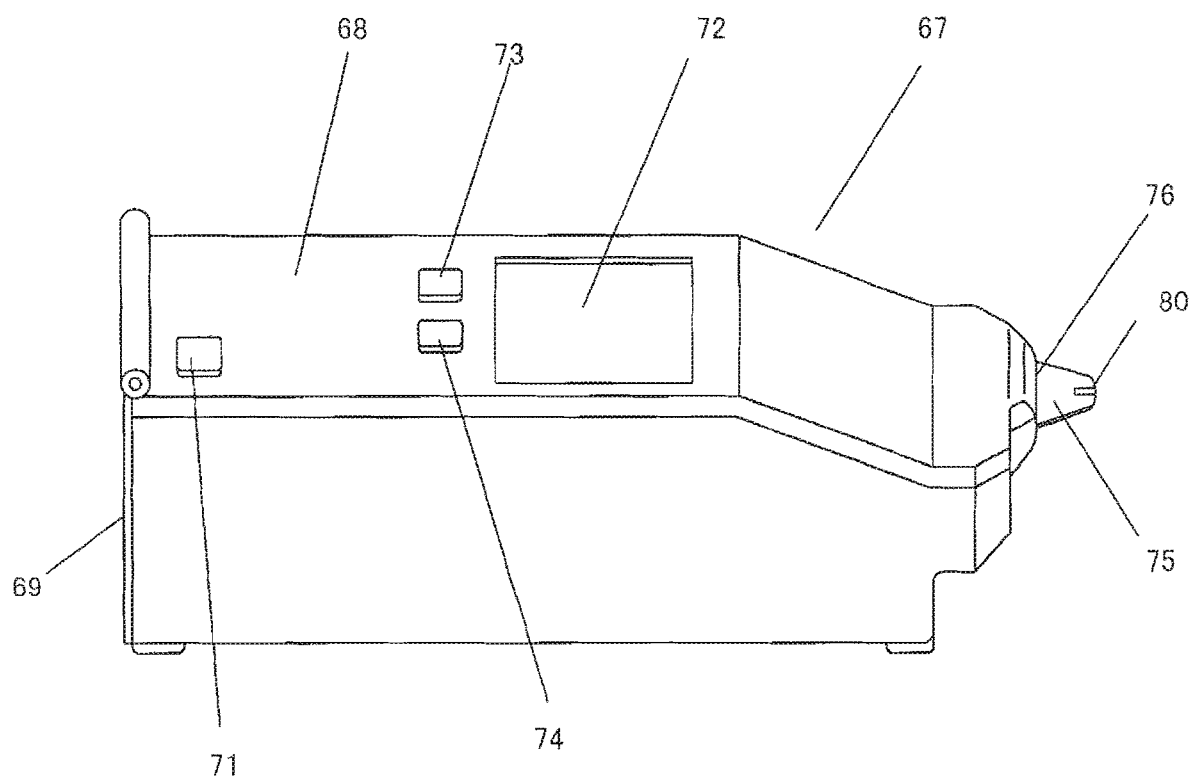
FIG. 25 is a perspective diagram of a biological information detection sensor feeding apparatus according to Embodiment 3.

FIG. 25 shows biological information detection sensor feeding apparatus 67 according to Embodiment 3. Biological information detection sensor feeding apparatus 67, which is used while being constantly placed on a planar surface such as for example, a desk, has a function to measure a blood glucose level (an example of biological information).

Figure 26:
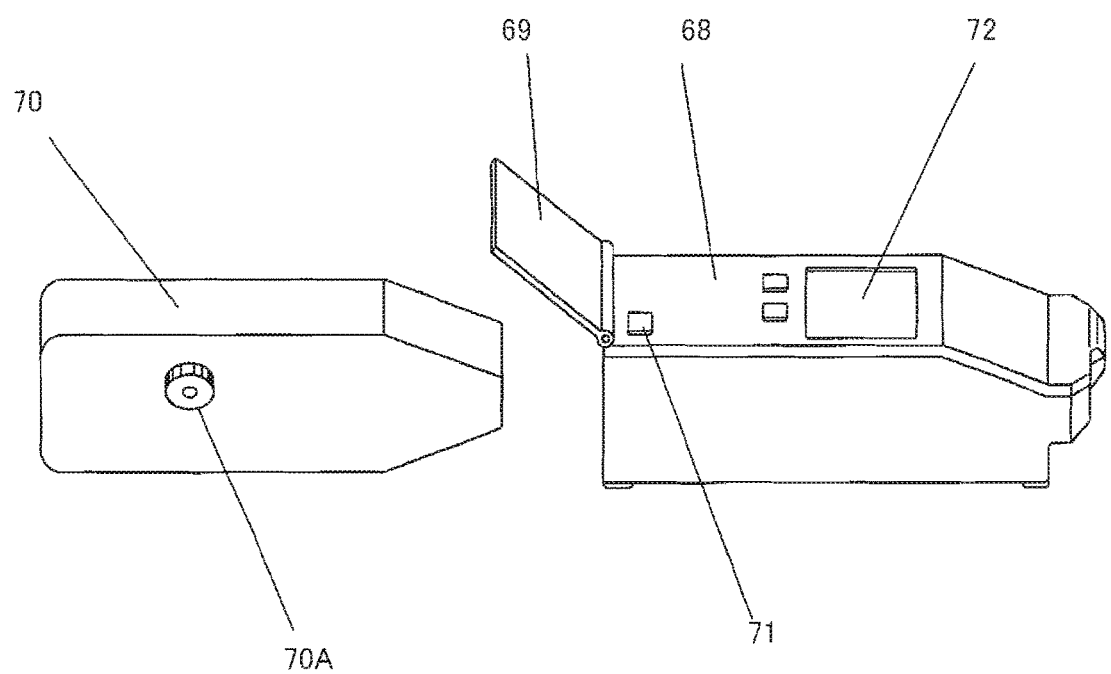
FIG. 26 is an exploded perspective diagram of the biological information detection sensor feeding apparatus according to Embodiment 3.

Biological information detection sensor feeding apparatus 67 has body case 68 molded in an approximately cuboidal shape. As shown in FIG. 26, biological information detection sensor feeding apparatus 67 is configured such that lid 69 at the rear end of body case 68 is opened and sensor cartridge 70 is stored in the interior thereof.

Power button 71 is provided at the rear end side of the upper surface of body case 68, and, displaying section 72, set button 73 for blood glucose sensor 75 (see FIG. 27) and disposition button 74 for blood glucose sensor 75 are provided at the center portion.

Once a user depresses power button 71 to turn the power on and thereafter depresses set button 73, blood glucose sensor 75 of sensor cartridge 70 is fed to loading opening 76 provided at the front-end surface of body case 68, as shown in FIG. 25 (the details will be described later).

Figure 27:
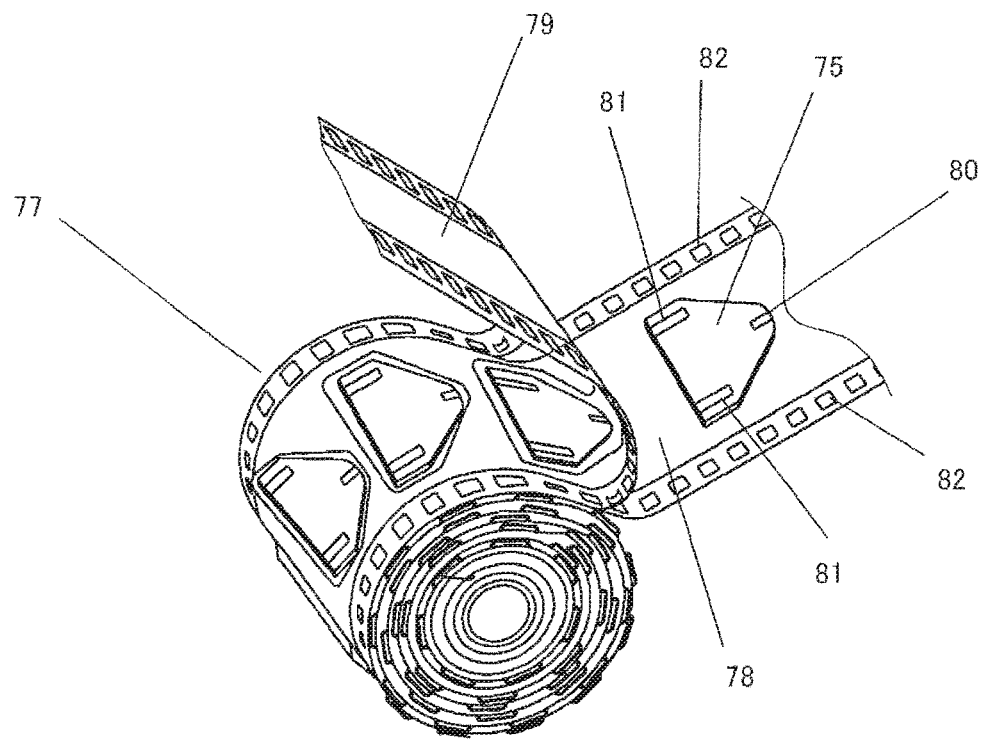
FIG. 27 is a perspective diagram of a sensor feeding film of the biological information detection sensor feeding apparatus according to Embodiment 3.

As shown in FIG. 27, blood glucose sensor 75 is stored in strip-shaped sensor feeding film 77. Sensor feeding film 77 includes strip-shaped holding film 78 and strip-shaped covering film 79 that covers a surface of this holding film 78.

Figure 29:
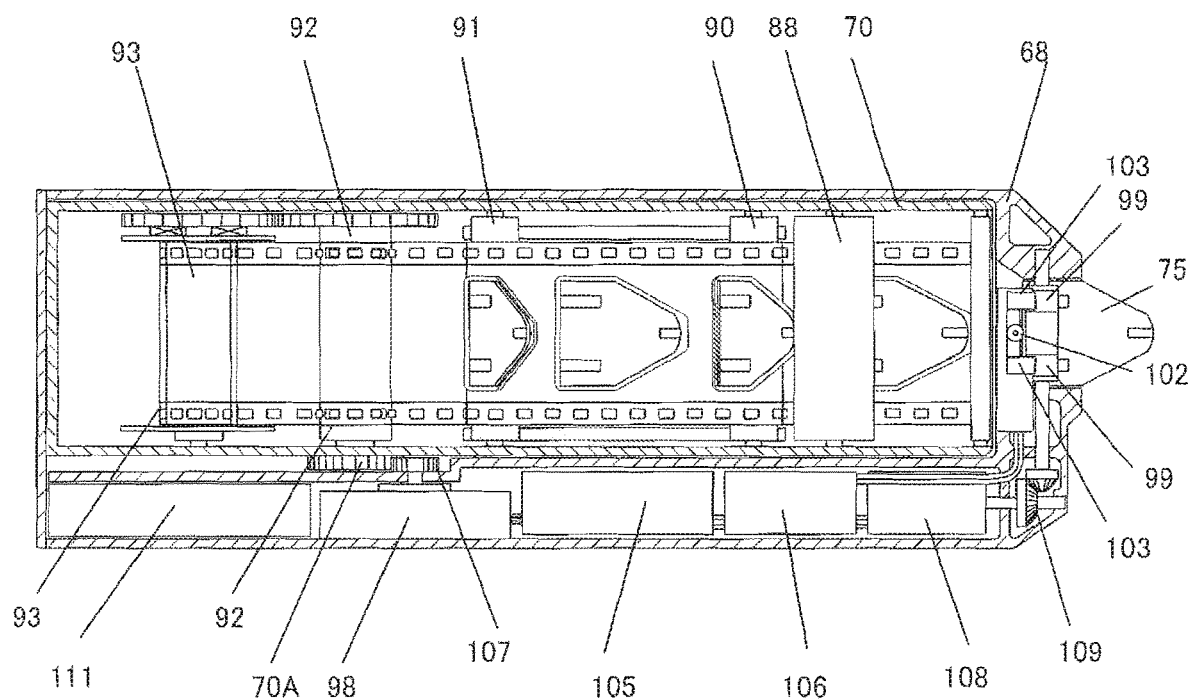
FIG. 29 is a perspective top diagram of the biological information detection sensor feeding apparatus according to Embodiment 3.

Blood glucose sensor 75 is disposed between strip-shaped holding film 78 and strip-shaped covering film 79. That is, on the surface of holding film 78, multiple (in the embodiment, 200) blood glucose sensors 75 are arranged at a predetermined interval along the longitudinal direction. Thus, blood glucose sensor 75 is held while being sandwiched between holding film 78 and covering film 79. As shown in FIG. 27 and FIG. 29, Embodiment 3 differs from the above-described Embodiment 1 in the orientation of blood glucose sensor 75 that is being stored in sensor feeding film 77, but has the same orientation as Embodiment 2.

Blood glucose sensor 75 has an approximately triangular and thin-plate shape. Spot-application portion 80 on which blood is to be spot-applied is provided near one apex of the triangle, and connecting electrodes 81 are provided from the end opposite to spot-application portion 80 to the center portion.

Feed guide holes 82 are provided at both ends in the direction orthogonal to the longitudinal direction of sensor feeding film 77. Feed guide holes 82 are holes for feeding sensor feeding film 77 to loading opening 76.

Figure 28:
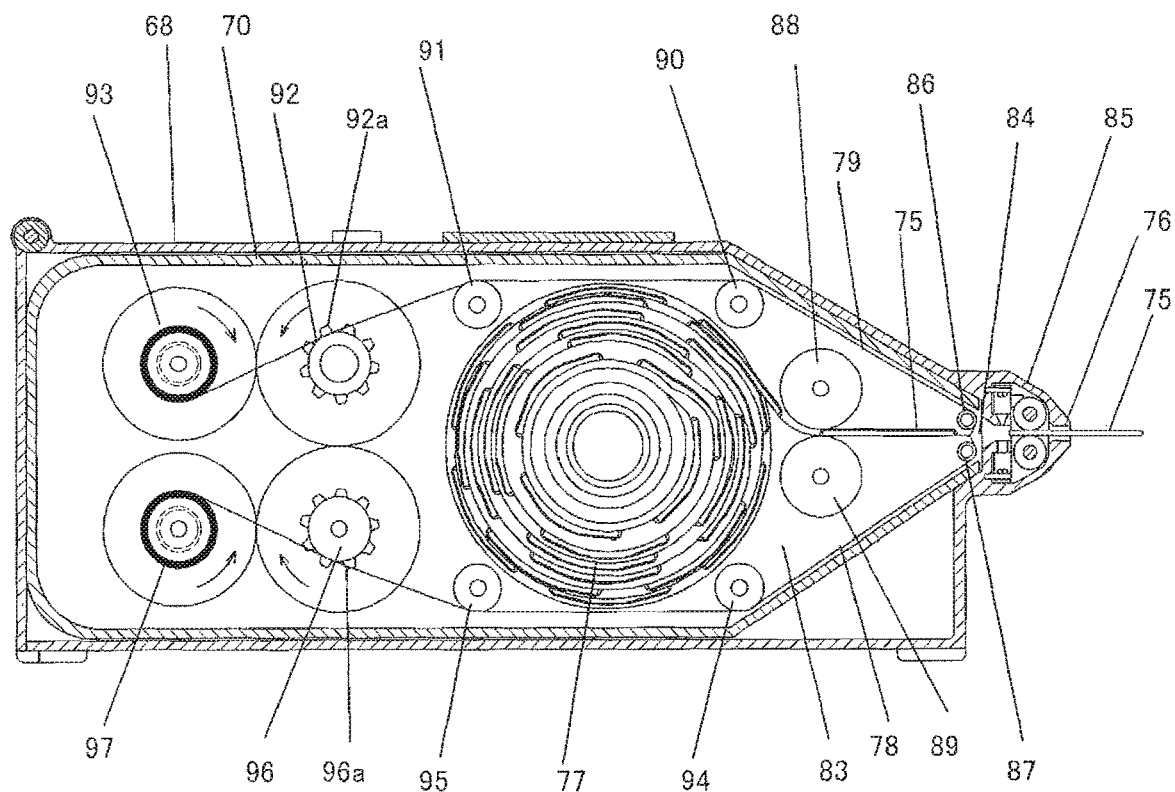
FIG. 28 is a lateral cross-sectional diagram of the biological information detection sensor feeding apparatus according to Embodiment 3.

Sensor feeding film 77 is stored in sensor cartridge 70 (FIG. 26). Furthermore, Sensor cartridge 70 is stored in body case 68. FIG. 28 is lateral a cross-sectional diagram of biological information detection sensor feeding apparatus 67 when sensor cartridge 70 is stored in body case 68, and FIG. 29 is an overhead cross-sectional diagram thereof.

The internal configuration of sensor cartridge 70 will be described. As shown in FIG. 28, a roll of sensor feeding film 77 is stored in storage section 83 provided at the center portion in the interior of sensor cartridge 70. Sensor feeding film 77 is loosely wound so that blood glucose sensor 75 held in sensor feeding film 77 is not damaged.

As shown in FIG. 28 and FIG. 29, the roll of sensor feeding film 77 is disposed such that the longitudinal direction of sensor feeding film 77 is oriented to the front-end of sensor cartridge 70. Sensor cartridge 70 is disposed such that feeding opening 84 thereof opposes loading opening 76.

As shown in FIG. 28, sensor feeding film 77, in which from the bottom in the drawing, holding film 78, blood glucose sensor 75 and covering film 79 are sequentially laminated, is fed toward feeding opening 84. Blood glucose sensor 75 is held in holding film 78, with spot-application portion 80 side being oriented to feeding opening 84.

Sensor loading section 85 for loading blood glucose sensor 75 is provided between feeding opening 84 of sensor cartridge 70 and loading opening 76.

In the interior of sensor cartridge 70, cylindrical separating pulleys 86, 87 are provided at portions opposite to feeding opening 84. Furthermore, a pair of cylindrical pressing pulleys 88, 89 is provided at the inward side of separating pulleys 86, 87 (at the upstream side in the feeding direction of sensor feeding film 77). The axial length of pressing pulleys 88, 89 is greater than the short-directional width of sensor feeding film 77. Therefore, pressing pulleys 88, 89 can press the whole of the short-directional width of sensor feeding film 77. Thereby, pressing pulleys 88, 89 correct peculiar windings of sensor feeding film 77 wound in a roll form, and then send it to separating pulleys 86, 87 at the downstream side.

Separating pulleys 86, 87 separate covering film 79 and holding film 78 from sensor feeding film 77.

Covering film 79 is returned upward and subsequently rearward by separating pulley 86, and through cylindrical guiding pulleys 90, 91 and cylindrical driving reel 92, is wound by cylindrical winding reel 93 (winding mechanism). As understood from FIG. 29, the axial lengths of separating pulley 86, guiding pulleys 90, 91 and driving reel 92 are greater than the short-directional width of sensor feeding film 77.

On the other hand, holding film 78 is returned downward and subsequently rearward by separating pulley 87, and through cylindrical guiding pulleys 94, 95 and cylindrical driving reel 96, is wound by cylindrical winding reel 97. The axial lengths of separating pulley 87, guiding pulleys 94, 95 and driving reel 96 are greater than the short-directional width of sensor feeding film 77.

Driving projections 92a, 96a are provided at both end sides of driving reels 92, 96. Driving projections 92a, 96a engage with feed guide holes 82 provided at both ends of sensor feeding film 77. Furthermore, driving reels 92, 96 are coupled with driving motor 98 (see FIG. 29) in body case 68 through connecting gear 70A (see FIG. 26).

That is, a winding mechanism for covering film 79 of sensor feeding film 77 is constituted by driving motor 98, connecting gear 70A, winding reel 93, driving reel 92, guiding pulleys 91, 90 and separating pulley 86.

A winding mechanism for holding film 78 of sensor feeding film 77 is constituted by driving motor 98, connecting gear 70A, winding reel 97, driving reel 96, guiding pulleys 95, 94 and separating pulley 87.

Winding reel 93 has the same slipping clutch mechanism as Embodiment 1, and is connected with driving reel 92. Winding reel 97 has the same slipping clutch mechanism as Embodiment 1, and is connected with driving reel 96.

Figure 30:
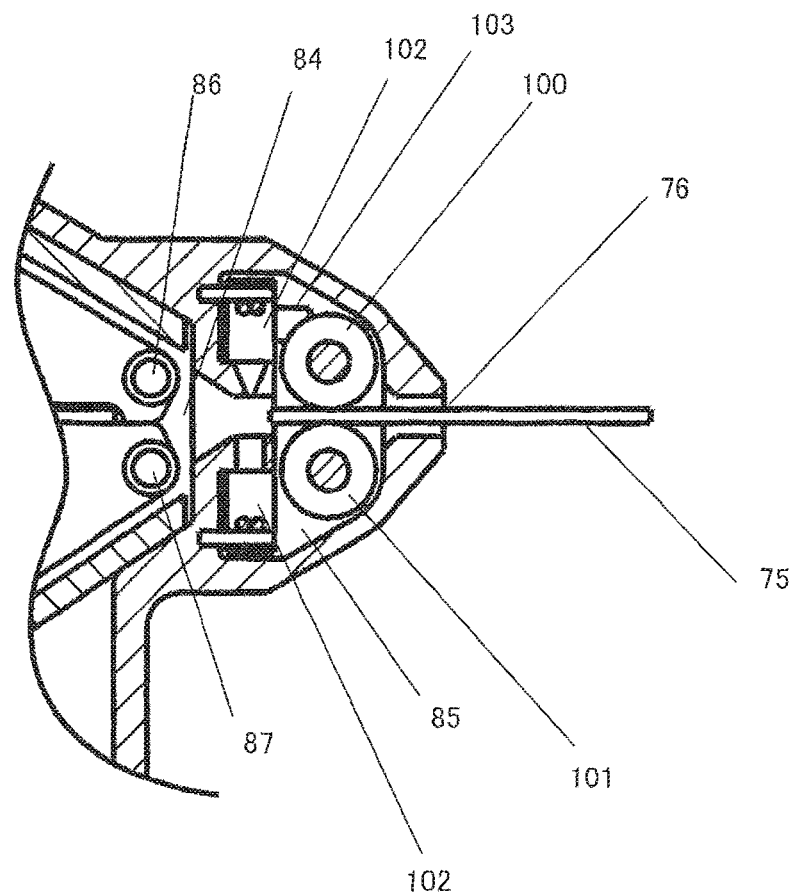
FIG. 30 is an enlarged lateral cross-sectional diagram of the principal part of a loading opening of the biological information detection sensor feeding apparatus according to Embodiment 3.

The internal configuration of body case 68 will be described. FIG. 30 is an enlarged lateral cross-sectional diagram of sensor loading section 85, and FIG. 31 is an enlarged overhead cross-sectional diagram of sensor loading section 85.

Figure 31:
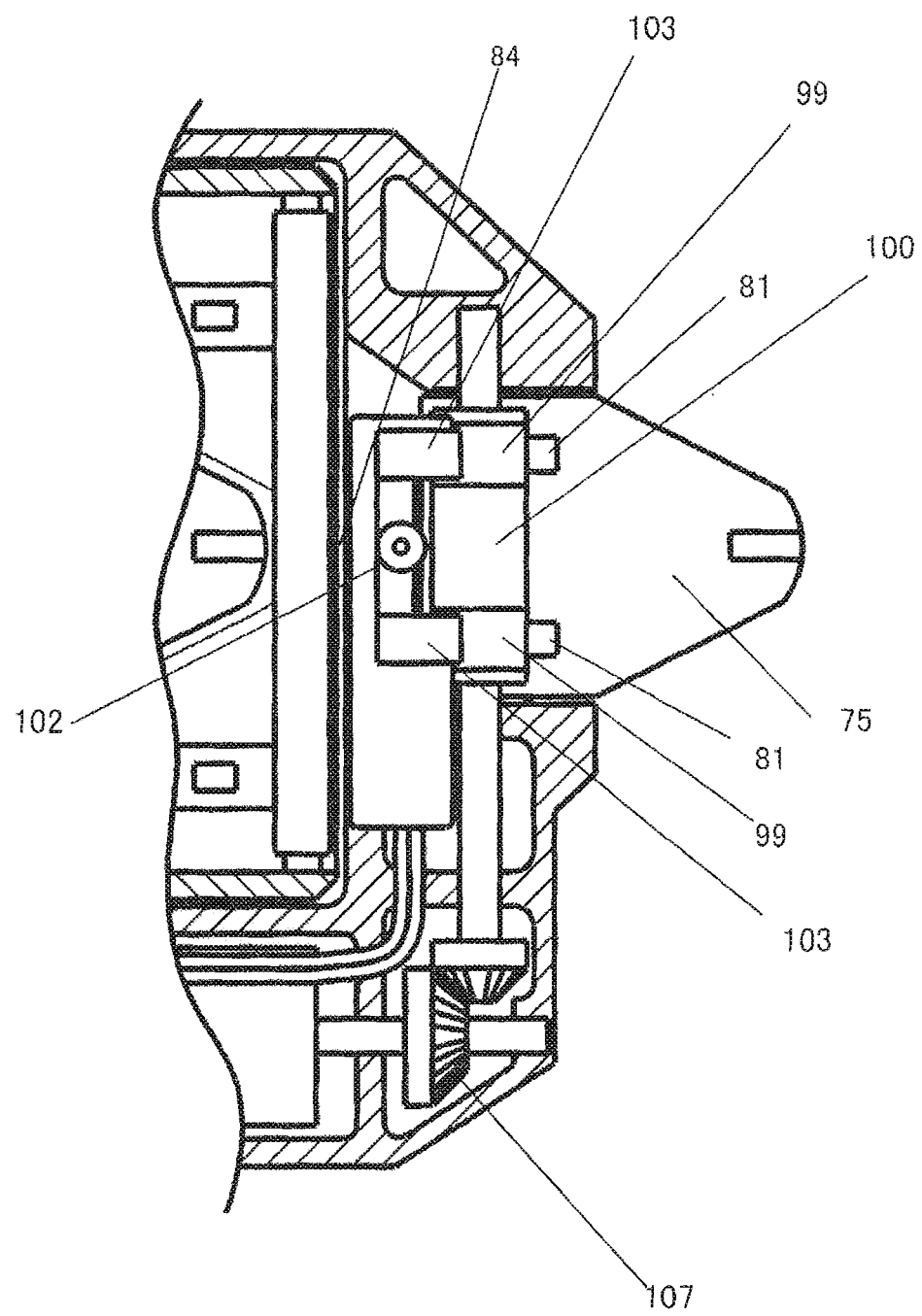
FIG. 31 is an enlarged perspective diagram of the principal part of the loading opening of the biological information detection sensor feeding apparatus according to Embodiment 3, viewed in the overhead direction.

As shown in FIG. 30 and FIG. 31, sensor loading section 85 has electrode roller 100 to be disposed on one surface side (the upper side in FIG. 30) of blood glucose sensor 75. Electrode roller 100 has roller electrodes 99 to be connected with connecting electrodes 81 of blood glucose sensor 75 (see FIG. 31). As shown in FIG. 31, roller electrodes 99 are provided on both end portions of the outer periphery of electrode roller 100.

Furthermore, as shown in FIG. 30, sensor loading section 85 has pressing roller 101 disposed on the other surface side (the lower side in FIG. 30) of blood glucose sensor 75. Pressing roller 101 presses blood glucose sensor 75 to electrode roller 100 side. For example, the rotating shaft portion of pressing roller 101 is pressed to electrode roller 100 side by a flat spring (an example of biasing member, not shown in the figure). When blood glucose sensor 75 is pressed onto electrode roller 100 by pressing roller 101, connecting electrodes 81 of blood glucose sensor 75 abut against and electrically connected to roller electrodes 99.

Optical sensor (an example of sensor detecting section) 102 is provided between feeding opening 84 and electrode roller 100. Optical sensor 102 detects blood glucose sensor 75 entered into sensor loading section 85.

As shown in FIG. 31, roller electrodes 99 contact with metallic connecting terminals 103. Roller electrodes 99 are connected with measuring section 104 (see FIG. 32) through metallic connecting terminals 103.

Figure 32:
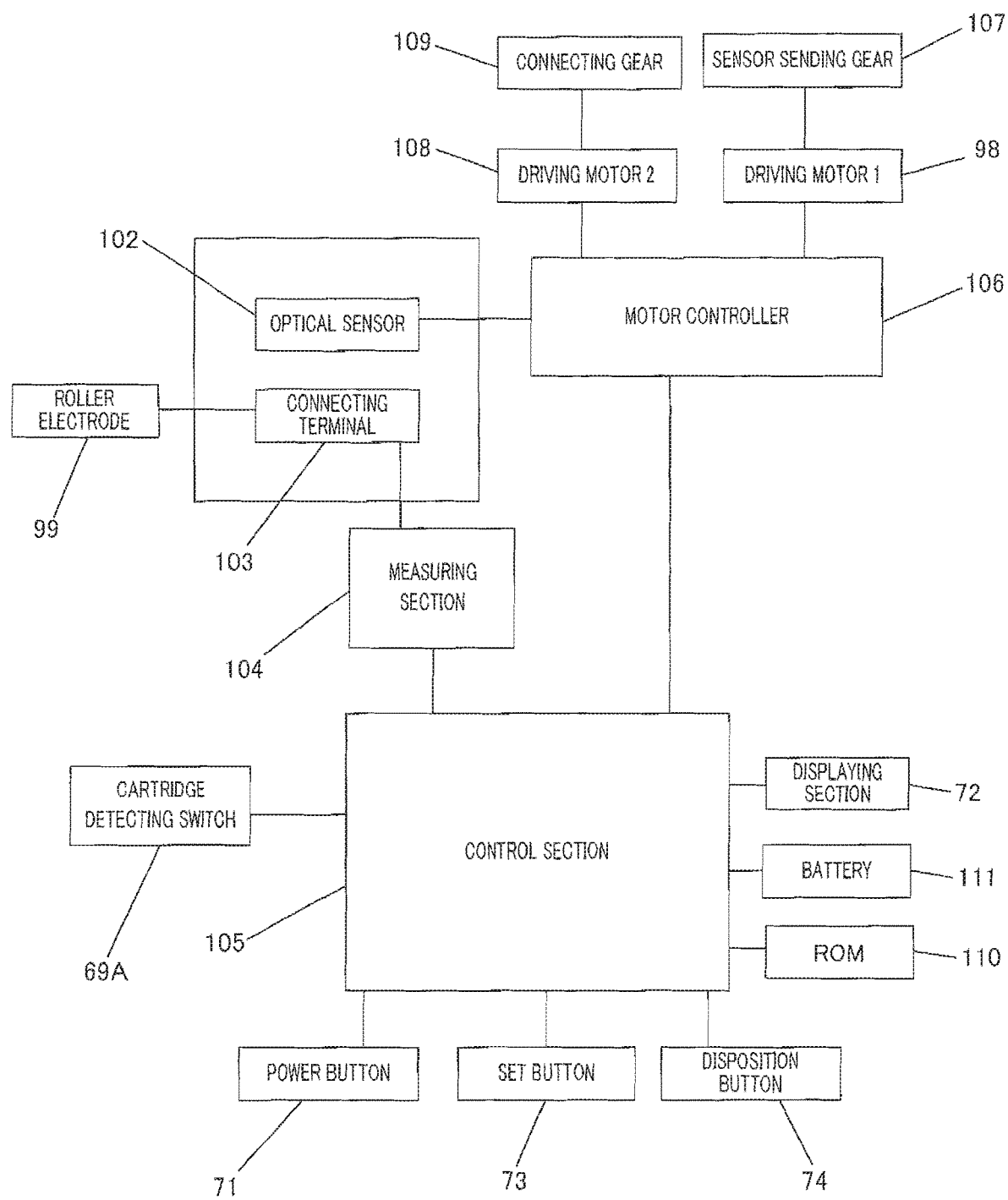
FIG. 32 is a control block diagram of the biological information detection sensor feeding apparatus according to Embodiment 3.

FIG. 32 is a control block diagram of biological information detection sensor feeding apparatus 67. Measuring section 104 is connected with control section 105. Control section 105 is connected with motor controller 106. Optical sensor 102 (see FIG. 30) is connected with motor controller 106. Optical sensor 102 and connecting terminals 103 (FIG. 29) are disposed on a printed board.

Driving motor 98 that drives connecting gear 70A of sensor cartridge 70 is connected with motor controller 106. The driving force of driving motor 98 is transmitted to sensor sending gear 107 (see FIG. 29) through connecting gear 70A of sensor cartridge 70, and further is transmitted to driving reel 92.

Furthermore, driving motor 108 that drives electrode roller 100 is connected with motor controller 106. The driving force of driving motor 108 is transmitted to electrode roller 100 through connecting gear 109, and electrode roller 100 transports blood glucose sensor 75.

In addition, cartridge detecting switch 69A that detects that sensor cartridge 70 has been stored in body case 68, ROM 110 in which programs in the control section are stored, battery 111, displaying section 72, power button 71, set button 73 for the sensor, and disposition button 74 for the sensor are connected with control section 105.

The operation of biological information detection sensor feeding apparatus 67 having the above configuration in use will be described hereinafter. First, as shown in FIG. 26, a user (a nurse) opens lid 69 at the rear end of body case 68, and loads sensor cartridge 70 to the interior of body case 68.

Next, once the user (nurse) depresses power button 71 (see FIG. 25) to turn the power on, control section 105 detects that sensor cartridge 70 is being loaded to body case 68, using cartridge detecting switch 69A. Thereafter, once the user (nurse) depresses set button 73 for the sensor, blood glucose sensor 75 of sensor cartridge 70 appears while being loaded into loading opening 76.

Specifically, control section 105 (see FIG. 30) that has detected the depression of set button 73, rotates driving motor 98 (see FIG. 29) by a predetermined amount, using motor controller 106. Then, the driving force of driving motor 98 is transmitted to driving reel 92 (see FIG. 28), through sensor sending gear 107 and connecting gear 70A.

Driving projections 92a of driving reel 92 transmit driving force to covering film 79 through feed guide holes 82 of covering film 79. As a result, covering film 79 is pulled out from storage section 83 to feeding opening 84 side by a predetermined amount corresponding to the rotation amount of driving motor 98, by the winding mechanism for covering film 79 (driving motor 98, connecting gear 70A, winding reel 93, driving reel 92, guiding pulleys 91, 90, and separating pulley 86).

Driving projections 96a of driving reel 96 transmit driving force to holding film 78 through feed guide holes 82 of holding film 78. As a result, holding film 78 is pulled out from storage section 83 to feeding opening 84 side by a predetermined amount corresponding to the rotation amount of driving motor 98, by the winding mechanism for holding film 78 (driving motor 98, connecting gear 70A, winding reel 97, driving reel 96, guiding pulleys 95, 94, and separating pulley 87).

That is, covering film 79 and holding film 78 are pulled out to feeding opening 84 side by the same predetermined amount. In other words, sensor feeding film 77 is pulled out by the predetermined amount. As described above, in this pulling-out, covering film 79 and holding film 78 are separated from sensor feeding film 77 by separating pulleys 86, 87. Then, one blood glucose sensor 75 is uncovered from holding film 78.

The biological information detection sensor feeding apparatus according to the embodiment is configured to automatically load blood glucose sensor 75 to loading opening 76. Specifically, first, by the driving force of separating pulleys 86, 87, uncovered blood glucose sensor 75 is entered into sensor loading section 85 through feeding opening 84 of sensor cartridge 70 (see FIG. 30).

Then, optical sensor 102 of sensor loading section 85 detects entered blood glucose sensor 75. Once optical sensor 102 detects blood glucose sensor 75, motor controller 106 drives driving motor 108. The driving force of driving motor 108 is transmitted to electrode roller 100 through connecting gear 109. Then, blood glucose sensor 75 reaches between electrode roller 100 and pressing roller 101. Thereafter, blood glucose sensor 75 is led to loading opening 76 by the driving force of electrode roller 100. Once blood glucose sensor 75 has been entered to a predetermined position, optical sensor 102 becomes unable to detect blood glucose sensor 75. At that time, motor controller 106 stops the driving of driving motor 108.

As shown in FIG. 31, roller electrodes 99 at both end portions of electrode roller 100 are abutted against and electrically connected to the connecting electrodes of blood glucose sensor 75 entered to the predetermined position. Thus, the loading of blood glucose sensor 75 into sensor loading section 85 is completed. Spot-application portion 80 of loading-completed blood glucose sensor 75 is in a state of being uncovered to the exterior of body case 68 through loading opening 76 (see FIG. 25).

A finger of a patient is punctured with a separately-prepared puncture instrument. Once the blood flowed out by puncturing is spot-applied on spot-application portion 80 of blood glucose sensor 75, the blood glucose level is measured by measuring section 104 and the result is displayed on displaying section 72.

Finally, the user (nurse) depresses disposition button 74. Control section 105 that has detected the depression of disposition button 74, rotates driving motor 98 using motor controller 106. Then, electrode roller 100 rotates and disposes blood glucose sensor 75 out of body case 68.

In the embodiment, driving motor 108 is coupled with electrode roller 100, but driving motor 108 only has to be coupled with at least one of electrode roller 100 and pressing roller 101.

As described above, biological information detection sensor feeding apparatus 67 according to the embodiment has the following features.

(1) Biological information detection sensor feeding apparatus 67 includes body case 68 having loading opening 76 for blood glucose sensor (biological information detection sensor) 75, storage section 83 that stores strip-shaped sensor feeding film 77 in body case 68, and the feeding section that feeds a predetermined length of sensor feeding film 77 from storage section 83 to loading opening 76.

Sensor feeding film 77 has strip-shaped holding film 78, strip-shaped covering film 79 covering the surface of holding film 78, and multiple blood glucose sensors 75 that are held by being sandwiched by holding film 78 and covering film 79.

The feeding section feeds a predetermined length of sensor feeding film 77 to feeding opening 84, and separates holding film 78 and the covering film from sensor feeding film 77 to uncover blood glucose sensor 75. The apparatus has a configuration in which uncovered blood glucose sensor 75 is fed to loading opening 76 through feeding opening 84.

Sensor loading section 85 into which blood glucose sensor 75 is to be loaded is provided between feeding opening 84 and loading opening 76. Sensor loading section 85 has electrode roller 100 and pressing roller 101. Electrode roller 100 is disposed on one surface side of blood glucose sensor 75, and has roller electrodes (connecting electrodes) 81 to be connected with connecting electrodes 81 of blood glucose sensor 75. Pressing roller 101 is disposed on the other surface side of blood glucose sensor 75, and is configured to press blood glucose sensor 75 to electrode roller 100 side.

(2) The apparatus has a configuration in which driving motor 108 is coupled with at least one of electrode roller 100 and pressing roller 101.

(3) The apparatus has a configuration in which optical sensor (sensor detecting section) 102 is provided between feeding opening 84 and electrode roller 100.

Thereby, once a user (nurse) depresses set button 73 for blood glucose sensor 75, holding film 78 and covering film 79 are separated from sensor feeding film 77, and one new blood glucose sensor 75 is uncovered. Furthermore, uncovered blood glucose sensor 75 can be loaded into sensor loading section 85. Spot-application portion 80 of blood glucose sensor 75 loaded into sensor loading section 85 protrudes from body case 68, and connecting electrodes 81 are connected with measuring section 104 through roller electrodes (connecting electrodes) 99. Thus, simply by depressing set button 73 for blood glucose sensor 75, the user (nurse) can load one new blood glucose sensor 75 into sensor loading section 85.

By spot-applying patient's blood on spot-application portion 80 of blood glucose sensor 75 loaded into sensor loading section 85, measuring section 104 measures the blood glucose level. As a result, the ease of use of biological information detection sensor feeding apparatus 67 increases.

INDUSTRIAL APPLICABILITY

The present invention is expected to be widely applied as a biological information detection sensor feeding apparatus that feeds a biological information detection sensor such as a blood glucose sensor, for example.

REFERENCE SIGNS LIST

1 Biological information detection sensor feeding apparatus
2 Body case
3 Blood glucose sensor
4 Feeding stage
4a Guiding section
4b Inclining portion
F Forefinger
5 Operating lever
6 Sensor feeding film
7 Holding film
8 Covering film
9 Feed guide hole
10 Storage section
11 Pressing pulley
12 Separating pulley
13, 14 Guiding pulley
15 Driving reel
15a Driving projection
16 Winding reel
17 Returning pulley
18, 19 Guiding pulley
20 Driving reel
20a Driving projection
21 Winding reel
22 Reel spindle
23 Gear
24 Spring retainer
25 Coil spring
26 Reeling part
27 Slipping member
28 Biological information detection sensor feeding apparatus
28a Attachment
28b Angle
28c End surface portion having an end surface
28d Lower-surface receiving portion of measurer
29 Measurer
29a Displaying section
29b Operating section
29c Case member
30 Blood glucose sensor
31 Feeding opening
32 Sensor loading section
32a Contact
33 Body case
34 Operating lever
35 Sensor feeding film
36 Holding film
37 Covering film
38 Spot-application portion
39 Connecting electrode
40 Feed guide hole
41 Storage section
42 Sensor feeding space
43 Sensor holding section
44, 45 Separating pulley
46, 47 Pressing pulley
48, 49 Guiding pulley
50 Driving reel
50a Driving projection
51 Winding reel
52, 53 Guiding pulley
54 Driving reel
54a Driving projection
55 Winding reel
56 Guiding opening
57 Sandwiching section
58, 59 Sandwiching claw
58a, 59a Abutting portion
60, 61 Rotating shaft
62 Spring
63, 64 Rotating cam
65 Connector
66 Guiding cutout
67 Biological information detection sensor feeding apparatus
68 Body case
69 Lid
69A Cartridge detecting switch
70 Sensor cartridge
70A Connecting gear
71 Power button
72 Displaying section
73 Set button
74 Disposition button
75 Blood glucose sensor
76 Loading opening
77 Sensor feeding film
78 Holding film
79 Covering film
80 Spot-application portion
81 Connecting electrode
82 Feed guide hole
83 Storage section
84 Feeding opening
85 Sensor loading section
86, 87 Separating pulley
88, 89 Pressing pulley
90, 91 Guiding pulley
92 Driving reel
92a Driving projection
93 Winding reel
94, 95 Guiding pulley
96 Driving reel
96a Driving projection
97 Winding reel
98 Driving motor
99 Roller electrode
100 Electrode roller
101 Pressing roller
102 Optical sensor
103 Connecting terminal
104 Measuring section
105 Control section 106 Motor controller
107 Sensor sending gear
108 Driving motor
109 Connecting gear
110 ROM
111 Battery

The invention claimed is:

1. A biological information detection sensor feeding apparatus comprising:
a measuring section that measures biological information;
a body case having a loading opening;
a sensor cartridge housed in the body case and housing a plurality of biological information detection sensors for detecting biological information, the sensor cartridge comprising:
 a storage section that stores a strip-shaped sensor feeding film in the sensor cartridge, the sensor feeding film including a biological information detection sensor, and a holding film and a covering film that sandwich the biological information detection sensor; and
 a feeding section that feeds the biological information detection sensor from the storage section to the loading opening of the body case;
a first drive motor that transmits a driving force via a connecting gear in the sensor cartridge;
a motor controller for rotating the first drive motor;
a cartridge detecting switch that is configured to detect the sensor cartridge stored in the body case; and
a control section that is configured to connect the measuring section, the motor controller and the cartridge detecting switch,
wherein:
the feeding section is configured to feed the biological information detection sensor on the sensor feeding film to the loading opening, and separate the holding film and the covering film from the sensor feeding film before feeding the biological information detection sensor to the loading opening;
the loading opening includes a connector connected with the measuring section and the biological information detection sensor includes a connecting electrode;
the feeding section is configured to feed the biological information detection sensor to the loading opening such that the connecting electrode of the biological information detection sensor is electrically connected with the connecter of the loading opening;
when the cartridge detecting switch detects that the sensor cartridge is loaded to the body case, the control section, by using the motor controller, rotates automatically the first drive motor by a predetermined amount, and the driving force of the first drive motor is transmitted to the feeding section via the connecting gear of the sensor cartridge, thereby feeding the biological information detection sensor to the loading opening of the body case.

2. The biological information detection sensor feeding apparatus according to claim 1, wherein:
the feeding section has a first winding mechanism that winds the covering film separated from the sensor feeding film, and second winding mechanism that winds the holding film separated from the sensor feeding film; and
each of the first winding mechanism and the second winding mechanism includes the first drive motor, the connecting gear and a clutch mechanism.

3. The biological information detection sensor feeding apparatus according to claim 1, wherein:
the biological information detection sensor has a spot-application portion on which a biological sample is to be spot-applied; and
the feeding section feeds the biological information detection sensor to the loading opening such that the spot-application portion is exposed.

4. The biological information detection sensor feeding apparatus according to claim 1, wherein the storage section of the sensor cartridge is configured to store the sensor feeding film, and the sensor cartridge is stored in the body case such that the cartridge is replaceable with a lid of body case being opened.

5. The biological information detection sensor feeding apparatus according to claim 1, wherein:
the loading section includes an electrode roller and a pressing roller, the electrode roller including a roller electrode connected with the measuring section; and
the feeding section is configured to feed the biological information detection sensor between the electrode roller and the pressing roller, and electrically connect the connecting electrode of the biological information detection sensor with the roller electrode of the electrode roller.

6. The biological information detection sensor feeding apparatus according to claim 5, wherein:
the main body case further includes a second drive motor connected to the motor controller,
the motor control is configured to drive the second drive motor, and
the driving force of the second drive motor is transmitted to the electrode roller.

7. A biological information detection sensor feeding apparatus comprising:
a body case having a loading opening; and
a sensor cartridge housed in the body case and housing a plurality of biological information detection sensors for detecting biological information,
wherein
the body case includes therein a control section that controls a motor controller connected to the control section, the motor controller drives a first drive motor connected to the motor controller, a cartridge detecting switch that is configured to detect the sensor cartridge stored in the body case, a set button for biological information detection sensor is provided at the surface of the body case, and the body case has an openable lid at a rear end thereof;
the sensor cartridge has a connecting gear for transmitting the driving force of the first driving motor on the side surface;
the sensor cartridge can be disposed inside the body case by opening the openable lid; and
when the cartridge detecting switch detects that the sensor cartridge is loaded to the body case, the control section, which has detected the depression of the set button, rotates the first driving motor by a predetermined amount by using the motor controller, then the driving force of the first driving motor is transmitted to the connecting gear of the sensor cartridge.

\* \* \* \* \*